(12) United States Patent
Yi et al.

(10) Patent No.: US 12,310,711 B2
(45) Date of Patent: May 27, 2025

(54) WEARABLE DEVICE AND METHOD FOR CONTROLLING THE SAME

(71) Applicants: KOREA INSTITUTE OF SCIENCE AND TECHNOLOGY, Seoul (KR); IUCF-HYU (Industry-University Cooperation Foundation Hanyang University), Seoul (KR)

(72) Inventors: Hyunjung Yi, Seoul (KR); Wonseop Hwang, Seoul (KR); Seongjin Park, Seoul (KR); Rhokyun Kwak, Seoul (KR); Jina Choi, Gwangmyeong-si (KR); Sangha Kim, Seoul (KR)

(73) Assignees: KOREA INSTITUTE OF SCIENCE AND TECHNOLOGY, Seoul (KR); IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 361 days.

(21) Appl. No.: 17/465,977

(22) Filed: Sep. 3, 2021

(65) Prior Publication Data
US 2023/0019206 A1   Jan. 19, 2023

(30) Foreign Application Priority Data
Jul. 16, 2021   (KR) .................. 10-2021-0093604

(51) Int. Cl.
*A61B 5/00*   (2006.01)
*A61B 5/0533*   (2021.01)
(Continued)

(52) U.S. Cl.
CPC ............ *A61B 5/0533* (2013.01); *A61B 5/352* (2021.01); *A61B 5/397* (2021.01); *A61B 5/4266* (2013.01); *A61B 5/6802* (2013.01)

(58) Field of Classification Search
CPC ....... A61B 5/0533; A61B 5/352; A61B 5/397; A61B 5/4266; A61B 5/6802; A61B 5/024;
(Continued)

(56) References Cited

U.S. PATENT DOCUMENTS

2014/0135636 A1*   5/2014   Kang ................... A61B 5/25
                                                                     600/509
2018/0146898 A1   5/2018   Begtrup et al.
(Continued)

FOREIGN PATENT DOCUMENTS

KR   1020190040610 A   4/2019
KR        101990894 B1   6/2019
(Continued)

OTHER PUBLICATIONS

Jessica Francis et al., "Digital nanoliter to milliliter flow rate sensor with in vivo demonstration for continuous sweat rate measurement," J. Name, 2013, 8 pages, The Royal Society of Chemistry.
(Continued)

*Primary Examiner* — May A Abouelela
(74) *Attorney, Agent, or Firm* — CANTOR COLBURN LLP

(57) ABSTRACT

A wearable device according to the present disclosure includes: a communication portion; a body fluid sensor configured to measure conductivity in body fluid; and a controller configured to control the communication portion to transmit conductivity data to an external device in response to the frequency of rapid change in the conductivity.

24 Claims, 27 Drawing Sheets

(51) Int. Cl.
*A61B 5/352* (2021.01)
*A61B 5/397* (2021.01)

(58) Field of Classification Search
CPC ... A61B 5/0205; A61B 5/0531; A61B 5/7285; A61B 5/14517; A61B 5/0002; A61B 5/02438; A61B 5/0537; A61B 5/1477; A61B 5/28; A61B 5/296; A61B 5/346; A61B 5/6833; A61B 10/0064
See application file for complete search history.

(56) References Cited

U.S. PATENT DOCUMENTS

| | | | |
|---|---|---|---|
| 2019/0082999 A1* | 3/2019 | Heikenfeld | A61B 5/7221 |
| 2020/0205673 A1* | 7/2020 | Yi | A61B 5/389 |
| 2021/0401346 A1* | 12/2021 | Visweswara | A61B 5/14507 |
| 2023/0098198 A1* | 3/2023 | Wang | A61B 5/4266 |
| | | | 600/307 |

FOREIGN PATENT DOCUMENTS

| | | |
|---|---|---|
| KR | 1020200075719 A | 6/2020 |
| KR | 102236245 B1 | 4/2021 |
| WO | 2018/017619 A1 | 1/2018 |

OTHER PUBLICATIONS

Yahui Yang et al., "Wearable microfluidics: fabric-based digital droplet flowmetry for perspiration analysis," Lab on a Chip, 2017, pp. 10 pages, The Royal Society of Chemistry.

* cited by examiner

WEARABLE DEVICE AND METHOD FOR CONTROLLING THE SAME

CROSS-REFERENCE TO RELATED APPLICATION

This application claims priority to and the benefit of Korean Patent Application No. 10-2021-0093604 filed in the Korean Intellectual Property Office on Jul. 16, 2021, the entire contents of which are incorporated herein by reference.

BACKGROUND

(a) Field of the Invention

The present disclosure relates to a wearable device and a control method thereof.

(b) Description of the Related Art

As the Internet of Things era where things and things or things and people are connected as arrived, the role of wearable devices is being emphasized. In line with this trend, wearable devices for measuring interaction between a body and the external environment are being studied.

Customized technology that measures biometric information non-invasively and long-term, efficiently manages personal health and adopts the measured biometric information to treatment based on the biometric information is in the spotlight as a technology that can change the paradigm of the future medical and health care industry. In particular, research on a skin attached sensor which is attached to skin to monitor a bio-signal is also being actively conducted. The bio-signal provides important information for biomedical devices, and multiple biosensors are essentially required to obtain individual signals from multiple points in a wide area.

There is a limit in battery capacity for down-sizing and weight reduction of the wearable device. There is also no adequate system to monitor a user's physical condition, and, if appropriate, to activate specific functions of the wearable device.

The above information disclosed in this Background section is only for enhancement of understanding of the background of the invention, and therefore it may contain information that does not form the prior art that is already known in this country to a person of ordinary skill in the art.

SUMMARY

The present disclosure is to provide a wearable device that reduces power consumption, and a control method thereof.

The present disclosure is to provide a wearable device with reduced storage capacity and a control method thereof.

The present disclosure is to provide a wearable device and a control method thereof that increase data processing efficiency.

The present disclosure is to provide a wearable device and a control method thereof that is adaptive to the user's physical condition.

However, the problems to be solved by the embodiments of the present invention are not limited to the above-described problems, and can be variously expanded in the range of technical ideas included in the present invention.

A wearable device according to an embodiment includes: a communication portion; a body fluid sensor configured to measure conductivity in body fluid; and a controller configured to control the communication portion to transmit conductivity data to an external device in response to the frequency of rapid change in the conductivity.

The controller may control the communication portion to transmit the frequency of rapid change in conductivity, and a maximum value and a minimum value in rapid change of the conductivity as the conductivity data to the external device.

The controller may control the communication portion to further include the entire conductivity values measured from when the frequency of rapid change of the conductivity increases in the conductivity data, and transmit them to the external device.

The wearable device may further include a bioelectric sensor that monitors at least one of an electrocardiogram (ECG) and an electromyogram (EMG).

The controller may control the bioelectric sensor to initiate monitoring with respect to at least one of the ECG and the EMG corresponding to the frequency of the rapid change in conductivity.

The controller may control the communication portion to extract R peak data in an ECG curve, measured by the bioelectric sensor, and transmit the extracted data to the external device, and may control the communication portion to transmit the ECG curve to the external device when the flow rate increases.

The wearable device may further include a pulse sensor that monitors a pulse.

The controller may control the pulse sensor to initiate monitoring of the pulse corresponding to the frequency of rapid change in conductivity.

When the frequency of rapid change in conductivity increases, the controller may control the communication portion to transmit the pulse data to the external device.

The body fluid sensor may include: an opening forming layer that includes a first side and a second side respectively facing opposite directions, and an opening penetrating from the first side to the second side in a thickness direction; a plurality of electrodes formed on an inner wall surface of the opening; and a hydrophilic layer stacked on the second side of the opening forming layer to cover the opening.

Each of the plurality of electrodes extends from the first side to the second side on the inner wall surface.

Each of the plurality of electrodes may be disposed at a predetermined height from the first side on the inner wall surface.

Any one of the plurality of electrodes may include an electrode that detects a specific component in the body fluid.

A control method of a wearable device according to an embodiment includes: measuring conductivity of a body fluid by a body fluid sensor; and transmitting conductivity data of the body fluid to an external device corresponding to a frequency of rapid change in conductivity.

The transmitting of the conductivity data of the body fluid may include transmitting the frequency of the rapid change in conductivity, and a maximum value and a minimum value of the conductivity as the conductive data to the external device, or when the frequency of the rapid change in conductivity is increased, transmitting the entire conductive values measured from when the frequency of the rapid change in conductivity increases, the frequency of the rapid change in conductivity, and the maximum and minimum values of the conductivity as the conductive data to the external device.

The control method of the wearable device may further include initiating monitoring with respect to at least one of an electrocardiogram (ECG) and an electromyogram (EMG)

corresponding to the frequency of the rapid change in conductivity by a bioelectric sensor.

The control method of the wearable device may further include: monitoring an ECG by a bioelectric sensor; and 1) extracting R peak data of an ECG curved line and transmitting the extracted data to the external device, or 2) when the frequency of the rapid change in conductivity increases, transmitting the ECG curve measured by the bioelectric sensor to the external device.

The control method of the wearable device may further include initiating monitoring with respect to a pulse corresponding to the frequency of the rapid change in conductivity by a pulse sensor.

The control method of the wearable device may further include: monitoring a pulse by a pulse sensor; and when the frequency of the rapid change in conductivity increases, transmitting pulse data to the external device.

The body fluid sensor may include: an opening forming layer that includes a first side and a second side respectively facing opposite directions, and an opening penetrating from the first side to the second side in a thickness direction; a plurality of electrodes formed on an inner wall surface of the opening; and a hydrophilic layer stacked on the second side of the opening forming layer to cover the opening, wherein the measuring of the conductivity in the body fluid by the body fluid sensor may include measuring a current flowing through the plurality of electrodes.

Calculating a flow rate of the body fluid from the conductive of the body fluid may include calculating a flow rate of the body fluid by using a frequency of rapid change in the conductivity, the volume of the opening, and the conductivity value.

A system according to an embodiment includes: a wearable device; and an electronic device that outputs data received from the wearable device.

When a frequency of rapid change in the conductivity increases, the wearable device may transmit conductivity data to the electronic device whenever the conductivity rapidly changes, and the electronic device may measure a flow rate of the body fluid by using a time point of receiving the conductivity data.

The wearable device may transmit a maximum value of the conductivity as the conductive data to the electronic device, and the electronic device may calculate an ion concentration of the body fluid by using a maximum value of the conductivity.

According to the present disclosure, the use time of the wearable device may be increased.

According to the present disclosure, wearable devices can be down-sized and thinned.

According to the present disclosure, a biological signal of a user can be continuously acquired for a long time by facilitating the collection and removal of bodily fluid.

According to the present disclosure, there is merit in easy data collection according to the user's physical condition.

According to the present disclosure, there is an effect of reducing manufacturing cost due to a small capacity memory.

DETAILED DESCRIPTION OF THE EMBODIMENTS

Figure 1:
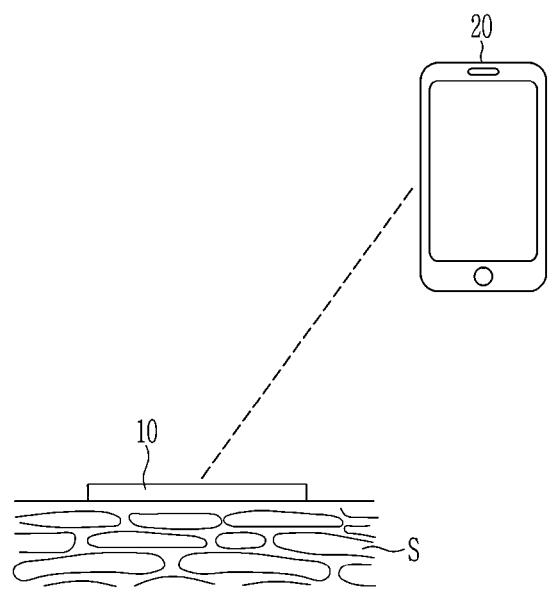
FIG. 1 exemplarily illustrates a wearable device and an electronic device according to an embodiment.

The present invention will be described more fully hereinafter with reference to the accompanying drawings, in which exemplary embodiments of the invention are shown. The drawings and description are to be regarded as illustrative in nature and not restrictive. Like reference numerals designate like elements throughout the specification. Further, some constituent elements in the accompanying drawings are exaggerated, omitted, or schematically illustrated, and a size of each constituent element does not fully reflect an actual size.

Further, the accompanying drawings are provided for helping to easily understand embodiments disclosed in the present specification, and the technical spirit disclosed in the present specification is not limited by the accompanying drawings, and it will be appreciated that the present invention includes all of the modifications, equivalent matters, and substitutes included in the spirit and the technical scope of the present invention.

Terms including an ordinary number, such as first and second, are used for describing various constituent elements, but the constituent elements are not limited by the terms. The terms are used only to discriminate one constituent element from another constituent element.

It will be understood that when an element such as a layer, film, region, or substrate is referred to as being "on" another element, it can be directly on the other element or intervening elements may also be present. In contrast, when an element is referred to as being "directly on" another element, there are no intervening elements present. Further, when an element is "on" a reference portion, the element is located above or below the reference portion, and it does not necessarily mean that the element is located "on" in a direction opposite to gravity.

In the present application, it will be appreciated that terms "including" and "having" are intended to designate the existence of characteristics, numbers, steps, operations, constituent elements, and components described in the specification or a combination thereof, and do not exclude a possibility of the existence or addition of one or more other characteristics, numbers, steps, operations, constituent elements, and components, or a combination thereof in advance. In the specification, unless explicitly described to the contrary, the word "comprise" and variations such as "comprises" or "comprising", will be understood to imply the inclusion of stated elements but not the exclusion of any other elements.

Further, throughout the specification, when it is referred to as "planar", it means the case where a target part is viewed from above, and when it is referred to as "in cross-section", it means the case where a cross-section obtained by vertically cutting the target part is viewed from the side.

Further, throughout the specification, when it is referred to as "connected", this does not only mean that two or more constituent elements are directly connected, but may mean that two or more constituent elements are indirectly connected through another constituent element, are physically connected, electrically connected, or are integrated even though two or more constituent elements are referred as different names depending on a location and a function.

FIG. 1 exemplarily illustrates a wearable device and an electronic device according to an embodiment. As shown in FIG. 1, the wearable device 10 may contact the user's skin S. The wearable device 10 may communicate directly with the electronic device 20 through a wired and/or wireless connection. In addition, the wearable device 10 may communicate with a network through a wired and/or wireless connection. The wearable device 10 may communicate with the electronic device 20 through a wired and/or wireless connection or through a network.

The wearable device 10 may perform an operation based on at least one biological or physiological characteristic of a user wearing the wearable device 10. Using at least one sensor, a processor, and codes executable on the processor, the wearable device 10 may be formed to detect and process wearer's physical characteristics such as gender, weight, height, body temperature, skin temperature, heart rate, respiration, blood sugar level, blood glucose level, stress/fatigue, electrical skin reaction, intake (protein), digestibility, metabolic rate, blood chemistry, sweat, deep and skin temperature, vital signs, dry eye, tooth decay, gum disease, energy storage, calorie combust speed, mental arousal, heart rhythm, sleep pattern, caffeine content, vitamin content, hydration, blood oxygen saturation, blood cortisol level, blood pressure, cholesterol, lactate level, body fat, protein level, hormone level, muscle mass, pH, etc., may be configured to detect and process characteristics, but not limited to, may detect and process other physical characteristics. Such a condition may also include a posture (e.g., supine, upright), movement, or a physical condition (e.g., sleep, exercise), and the like, but is not limited thereto.

The wearable device 10 is a haptic output device (e.g., an offset motor, an electroactive polymer, a capacitive voltage generator, a Peltier temperature element, a shrink material, braille coding actuators), a telemetry device, a visual device, an audible device, and other output device including, but may include at least one output device not limited thereto.

The wearable device 10 may include artificial intelligence so that the wearable device 10 can learn and adapt to individual wearers. The wearable device 10 can be configured to accurately distinguish between an erroneous (accidental, unintentional, and the like.) input and a valid sensor input, and thus accurate conclusions can be drawn about the wearer's physical condition or characteristic (e.g., wearable device 10 does not interpret a wearer who rolls in motion while sleeping as a wearer in motion). The wearable device 10 may also include at least one camera or other visual sensor for recognizing a face, user, or other image. The wearable device 10 may also be configured to send information to and/or retrieve information from a wearer's digital health history.

The wearable device 10 may be formed to output information to a user, to another wearable device 10, to an electronic device 20, or to a network according to specific features and functions of the device.

The electronic device 20 may be any conventional "smart" device with a processor, an associated operating system, and a communication interface. The electronic device 20 may include a smartphone, a tablet computer, a laptop computer, a desktop computer, and a set-top box.

Figure 2:
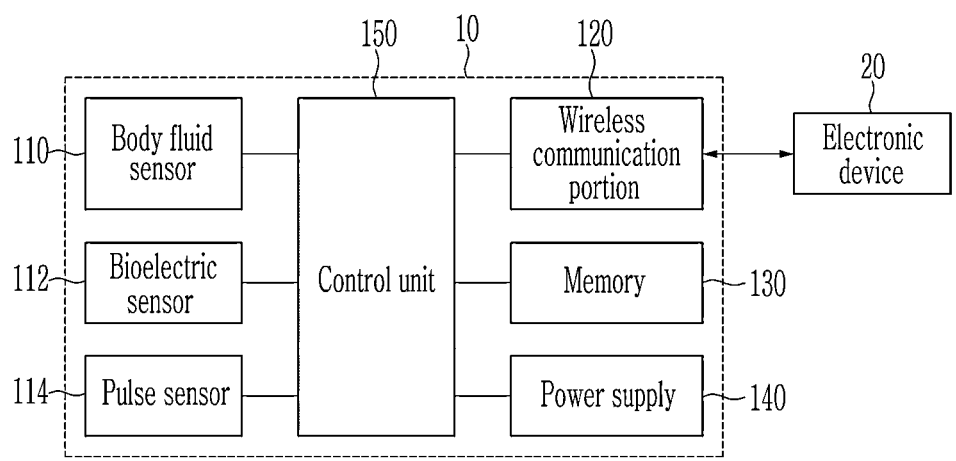
FIG. 2 is a block diagram of the wearable device and the electronic device according to the embodiment.

FIG. 2 is a block diagram of the wearable device and the electronic device according to the embodiment.

As shown in FIG. 2, the wearable device 10 includes a sensor for detecting biological or physiological characteristics, such as a body fluid sensor 110, a bioelectric sensor 112, and a pulse sensor 114, a wireless communication portion 120, a memory 130, a power supply 140, and a controller 150.

The body fluid sensor 110 may detect the user's body fluid. The body fluid sensor 110 is a sensor for analyzing the body fluid discharged from the user's skin S. The body fluid sensor 110 may, for example, detect and monitor sweat discharged through sweating through the sweat glands of the user's skin.

The body fluid sensor 110 may include at least one opening for discharging body fluid in a direction away from the user's skin. For example, when sweat is discharged through the sweat glands of the user's skin, the opening of the body fluid sensor 110 may be used as a passage through which the sweat discharged through the sweat glands of the user's skin moves.

The body fluid sensor 110 may include an electrode for detecting a current flowing through the user's body fluid present in the opening.

While the sweat discharged through the sweat glands of the user's skin moves through the opening, the electrode of the body fluid sensor 110 may sense the current flowing through the sweat. The current flowing through the sweat sensed by the body fluid sensor 110 can be used to generate sensing data.

The opening may have a predetermined shape in which sweat discharged through the sweat glands of the user's skin can be discharged by effectively moving in a direction away from the user's skin. In addition, the opening may have a predetermined shape capable of effectively detecting a current flowing through the sweat. The opening, for example, may have a shape in which the circumference decreases as the distance from the skin attachment surface increases.

The bioelectrical sensor 112 may monitor an electrophysiological signal of a user. The bioelectric sensor 112 may detect and monitor, for example, at least one of an electrocardiogram (ECG) and an electromyogram (EMG) by detecting a microcurrent flowing through the user's body.

The bioelectric sensor 112 may include a hydrogel having a lower portion in contact with the user's skin to absorb moisture generated from the user's skin.

Hydrogel is also called waterized gel, and has a network structure that forms three-dimensional crosslinks by physical (hydrogen bonding, van der Waals force, hydrophobic interaction, or polymer crystals) or chemical (covalent bonding) bonding of water-soluble polymers, and it does not dissolve in an aqueous environment and has pores inside such that it may mean a material that can contain a significant amount of water.

The hydrogel that can be used in the bioelectric sensor of the present disclosure is a conductive hydrogel that can transmit an electrical signal of a living body, and may be used as an electrode for medical devices such as an electrocardiogram (ECG) electrode, an electroencephalogram (EEG) electrode, an electromyogram (EMG) electrode, a transcutaneous electrical nerve stimulator (TENS), a electrosurgery unit (ESU) ground electrode, and the like.

Since hydrogels can be made from various water-soluble polymers, and they have various chemical compositions and physical properties. In addition, it is easy to process and has merit that it can be transformed into various shapes depending on the application.

A hydrogel containing a specific amount of moisture can absorb moisture generated from the user's skin and thus its volume may be relatively increased. On the contrary, a hydrogel containing a predetermined amount of water may have a relatively reduced volume as water evaporates through the surface of the hydrogel.

The bioelectric sensor 112 may include an electrode for sensing a current flowing through the hydrogel from the user's skin. While the moisture discharged through the user's skin is absorbed by the hydrogel, the electrode of the bioelectric sensor 112 can sense the current flowing through the hydrogel from the user's skin. The current sensed by the bioelectric sensor 112 can then be used to generate sensing data.

The bioelectric sensor 112 may include an elastic body membrane in contact with an upper portion of the hydrogel. The elastic body membrane may include at least one opening. As the volume of the hydrogel increases, a circumference of each opening is stretched to release the water absorbed by the hydrogel.

The pulse sensor 114 may monitor the user's pulse. The pulse sensor 114 may include, for example, a strain sensor or a pressure sensor that detects a change in skin in contact with a pulse position.

A strain sensor is a sensor that detects a minute mechanical strain by converting it into an electrical signal. For example, when the strain sensor is attached to the user's skin surface, it becomes possible to measure a change in minute dimensions occurring on the skin surface, and the user's pulse can be obtained from a size and a cycle of the measured strain.

The pressure sensor is a sensor that detects a minute change in pressure applied to the sensor by converting it into an electrical signal. For example, in the case of a pulse, a pressure of several to tens of kPa can be applied to the device, and thus when the user attaches a pressure sensor to the skin surface, minute pressure strains can be measured due to the pulse, and the user's pulse can be obtained from a size and a cycle of the measured strain.

In addition, the wearable device 10 may include a biological sensor that can measure at least one of blood sugar, stress, fatigue, anxiety, arousal, heart rate, electrical skin reaction, weight, nutrition, digestibility, metabolic rate, body temperature, skin temperature, respiration, allergy, sleep pattern, hydration, drug level, sweat generation, and blood analysis, a temperature sensor, an altitude sensor, a motion sensor, a position sensor, and other sensors capable of performing the functions described herein, but this is not restrictive.

A typical wireless communication portion 120 (e.g., a transmitter or receiver or transceiver) may be included if necessary to perform one or more of the functions of the smart wearable device described herein. Examples of wireless communication capabilities that may be provided include, but are not limited to, Bluetooth, Wi-Fi, infrared, cellular, and near field communication.

A memory 130 may include any suitable conventional RAM type of memory and/or ROM type of memory.

The power supply 140 receives external and internal power under the control of the controller 150 and supplies power to each constituent element included in the wearable device 10. The power supply 140 includes a battery, and the battery can be a built-in battery or a replacement battery.

The controller 150 may be any suitable conventional processor. The controller 150 generally controls the overall operation of the wearable device 10 in addition to the operation related to the application program. The controller 150 can provide or process appropriate information or functions to the user by processing signals, data, information, and the like input or output through the constituent elements described above or by driving an application program stored in the memory 130.

In addition, the controller 150 may control at least a part of the constituent elements described with reference to FIG. 2 to drive an application program stored in the memory 130. Furthermore, the controller 150 may operate by combining at least two or more of the constituent elements included in the wearable device 10 with each other in order to drive the application program.

In addition, the wearable device may include an interface unit capable of communicating with an external electronic device 20 and/or a network.

Next, wearing of the wearable device will be described in more detail with reference to FIG. 3.

Figure 3:
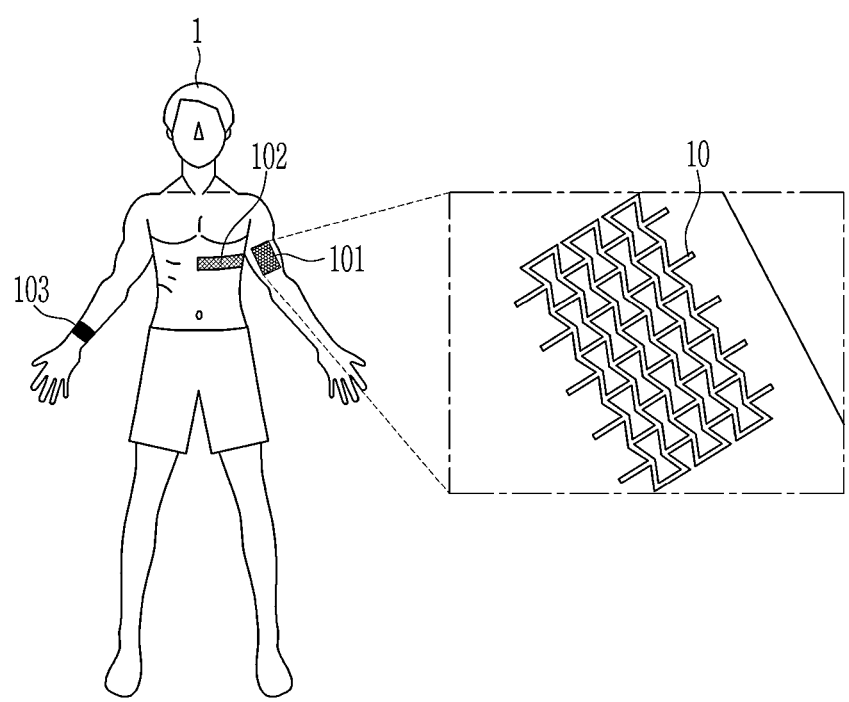
FIG. 3 exemplarily illustrates wearing of the wearable device according to the embodiment

FIG. 3 exemplarily illustrates wearing of the wearable device according to the embodiment.

Referring to FIG. 3, the wearable device 10 may be attached to the body of a user 1. The wearable device 10 can be freely attached to a part of the user's body surface according to the object to be measured or detected.

For example, the wearable device 10 can be attached to an arm of the user 1 and used for EMG measurement and body fluid detection of the user 1. The wearable device 10 is attached to the chest of the user 1 and can be used to measure an electrocardiogram and detect body fluids of the user (102). The wearable device 10 is attached to a wrist of the user 1 and can be used to measure the pulse and detect body fluids of the user 1 (103).

In addition, the wearable device 10 may be implemented as a hand worn device, a finger worn device, a wrist worn device, a head worn device, an arm worn device, a leg worn device, an ankle worn device, a foot worn device, and a toe worn device, wrist watch, glasses, ring, bracelet, necklace, jewellery, clothing, shoes, hat, contact lens, gloves, and the like, which can contact the skin of the user 1, but is not limited thereto.

Figure 4:
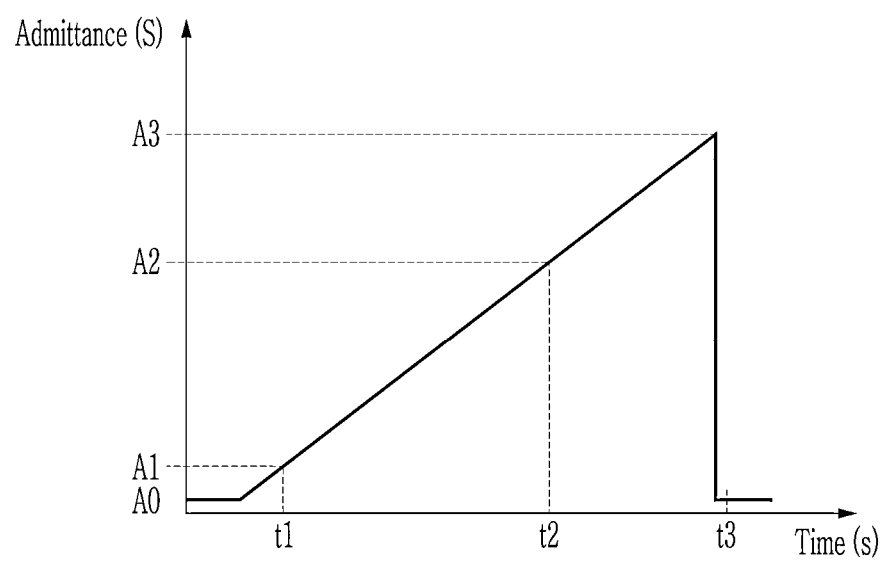
FIG. 4 is a graph that shows admittance measurement values according to body fluid collection of the body fluid sensor of the wearable device according to the embodiment.
Figure 5:
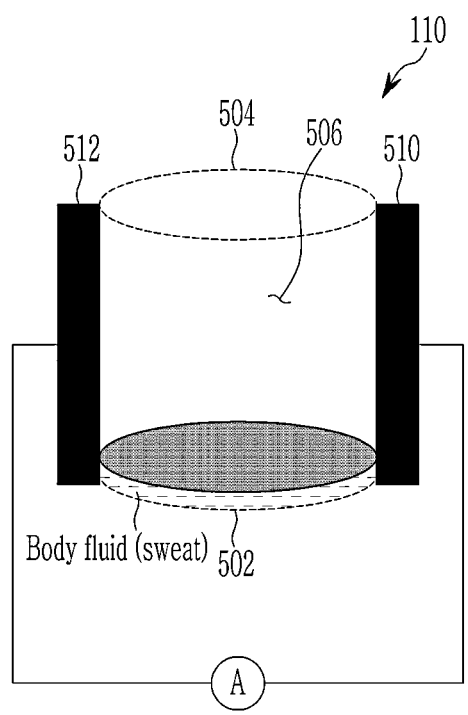
FIG. 5 to FIG. 7 exemplarily illustrate examples of body fluid collection of the body fluid sensor of the wearable device according to the embodiment.
Figure 6:
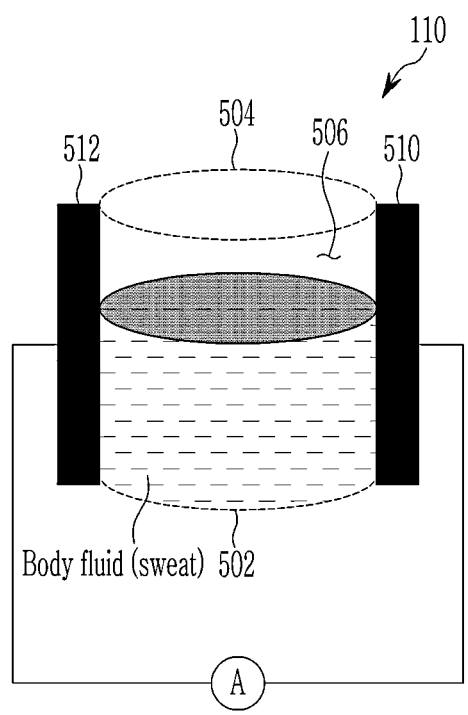
Figure 7:
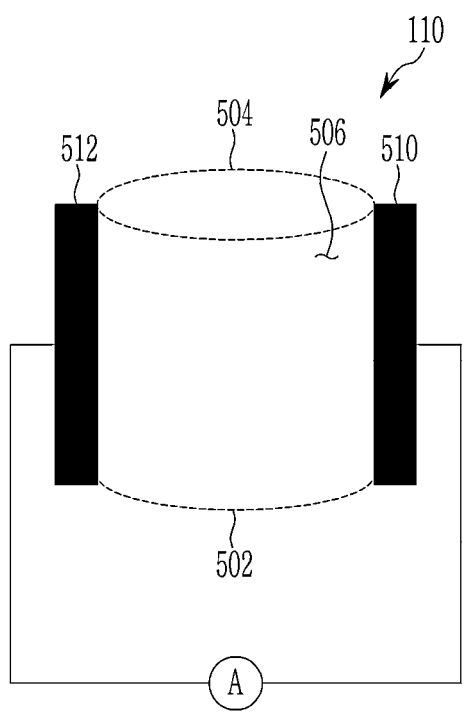

FIG. 4 is a graph that shows admittance measurement values according to body fluid collection of the body fluid sensor of the wearable device according to the embodiment, and FIG. 5 to FIG. 7 exemplarily illustrate examples of body fluid collection of the body fluid sensor of the wearable device according to the embodiment.

Referring to FIG. 4, as the body fluid (e.g., sweat) of the user 1 is discharged from the skin S, the admittance measured by the body fluid sensor 110 increases (A0-A1-A2-A3), and then when the body fluid is discharged, the admittance drops sharply (t3). Here, the body fluid sensor 110 is described as measuring the admittance of a body fluid, but the body fluid sensor 110 can measure the amount of body fluid perspiration, ion concentration in the body fluid, and the like as a unit for measuring the conductivity between two electrodes, and conductivity can be measured with impedance, resistance, and the like, but is not limited thereto.

FIG. 5 illustrates the body fluid sensor 110 collected the body fluid at t1. The body fluid is discharged from the skin S, and may be collected in an opening 506 through a first surface 502 of the body fluid sensor 110.

The opening 506 may be penetrated in a thickness direction from a first side 502 to a second side 504. Here, the first surface 502 may be a surface attached to the skin S of the user 1, and the second surface 504 may be a surface facing the outside. Accordingly, the opening 506 may provide a passage through which sweat collected from the first side 502 attached to the skin S is discharged to the second side 504.

A plurality of electrodes 510 and 512 spaced apart from each other may be disposed on the inner wall surface of the opening 506. In the following drawing, the two electrodes 510 and 512 for measuring current on an inner wall surface of the opening 506 are shown to be disposed to face each other, but the two electrodes 510 and 512 may be disposed adjacent to each other and alignment of the electrodes within the wall is not limited.

The body fluid sensor 110 may determine the amount of body fluid discharged from the user's skin S based on an increase in the height of the body fluid present in the opening 506. The electrodes 510 and 512 of the body fluid sensor may have a nano-network structure, the nano-network structure has high capacitance, and thus a more sensitive body fluid sensor may be implemented due to a large current change according to a change in body fluid.

The body fluid sensor 110 may measure admittance A1 by measuring a current flowing through the body fluid collected in the two electrodes 510 and 512 and the opening 506. FIG. 6 illustrates the body fluid sensor 110 collected the body fluid at t2. The height of the bodily fluid present in the opening 506 may increase with the passage of time or according to the physical condition of the user 1. The body fluid increases in height towards the second side 504 of the body fluid sensor 110.

The bodily fluid is gradually collected in the opening 506, and as the amount of the bodily fluid in the opening 506 increases, the admittance values measured by the two electrodes 510 and 512 increase from A1 to A2 and from A2 to A3. A maximum value A3 of the admittance is measured before the body fluid collected in the opening 506 is removed.

FIG. 7 illustrates the body fluid sensor 110 after the body fluid at t3 is discharged. The bodily fluid in the opening 506 is discharged to the outside of the opening 506 through the second surface 504. Then, the value of the measured admittance drops sharply to a minimum value A0. Here, the minimum value A0 may be measured as a different value depending on the ion concentration of the body fluid. For example, the minimum value A0 when the ion concentration of a body fluid is high is greater than the minimum value A0 when the ion concentration of the body fluid is low. In addition, the minimum value A0 may be measured as a different value depending on the amount of body fluid remaining in the opening 506. For example, the greater the amount of body fluid remaining within the opening 506, the greater the size of the minimum A0. In addition, the minimum value A0 may be measured to be zero when there is no body fluid remaining in the opening 506.

As the body fluid is discharged, a sharp change in admittance occurs. Accordingly, whenever the admittance measured by the body fluid sensor 110 rapidly changes, a flow rate of the body fluid may be calculated as the volume of the opening 506 (or a predetermined volume less than the volume of the opening 506) is discharged. Specifically, the flow rate of the body fluid may be calculated based on a difference between the maximum value A3 and the minimum value A0, the ratio of the maximum value A3, and the volume of the opening 506. For example, when the maximum value A3 measured when the current admittance suddenly changes is 3000 (S) and the minimum value A0 is 600 (5), the difference between the maximum value A3 and the minimum value A0 is 2400 (S). This is 80% of the maximum value A3, and the flow rate of the body fluid discharged when the current admittance is rapidly changed may be calculated as 80% of the volume of the opening 506. Therefore, when the maximum and minimum values are measured during a sudden change in the body fluid, the controller 150 or the electronic device 20 may calculate the frequency of the sudden change of the body fluid and the flow rate of the body fluid based on these values.

In addition, the controller 150 may calculate the flow rate of the body fluid whenever the admittance measured by the body fluid sensor 110 rapidly changes. Alternatively, whenever the admittance measured by the body fluid sensor 110 rapidly changes, the external electronic device 20 may receive a signal from the wearable device 10 and calculate the flow rate of the body fluid using the signal reception timing. In this case, the wearable device 10 may transmit the maximum value A3 and the minimum value A0 of the admittance measured before and after the timing at which the admittance is rapidly changed to the external electronic device 20 as signals. In addition, the wearable device 10 may transmit the maximum value of admittance and the difference between the maximum value and the minimum value (A3-A0) and the ratio (A3/(A3-A0)) of the maximum value A3 to the external electronic device 20 as a signal.

The change in the measured admittance will now be described with reference to FIG. 8 to FIG. 11.

FIG. 8 to FIG. 11 are graphs that show the change of admittance measurement value according to the body fluid collection of the body fluid sensor of the wearable device according to the embodiment.

Figure 8:
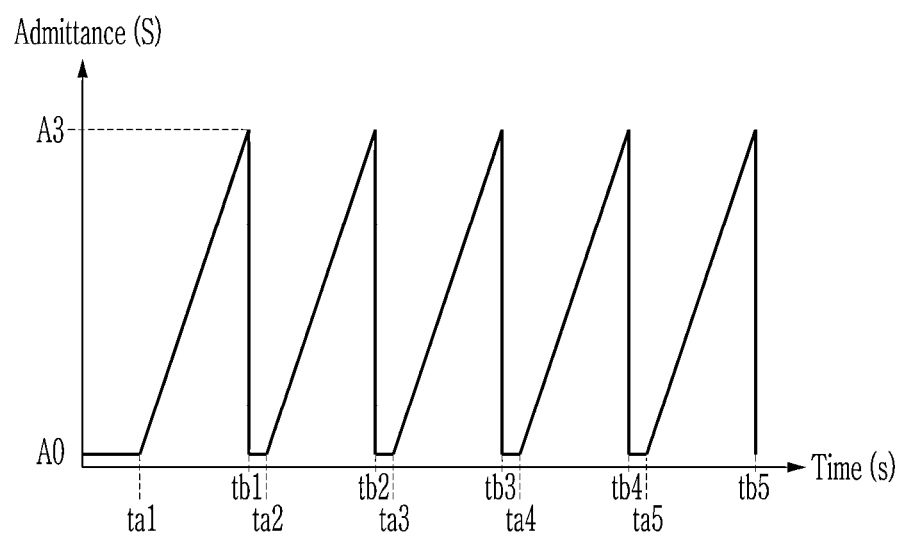
FIG. 8 to FIG. 11 are graphs that show the change of admittance measurement value according to the body fluid collection of the body fluid sensor of the wearable device according to the embodiment.
Figure 9:
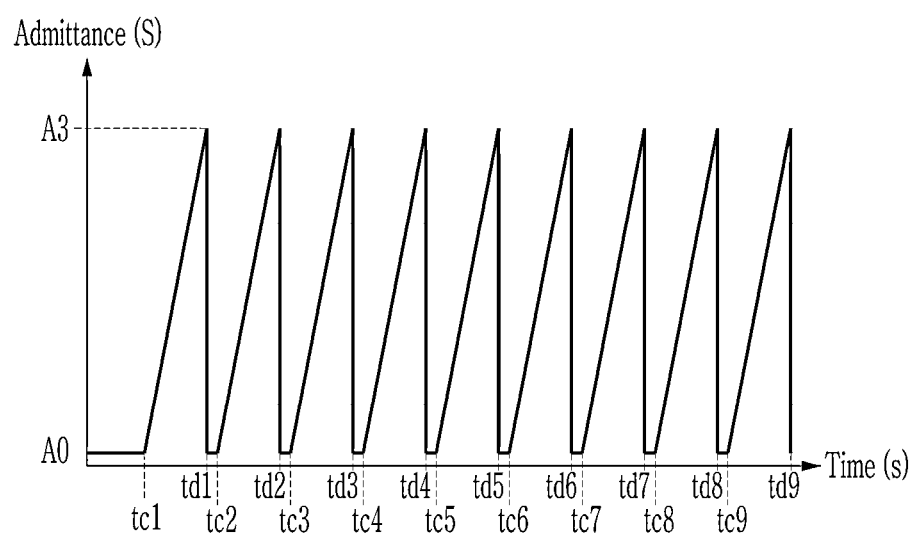
Figure 10:
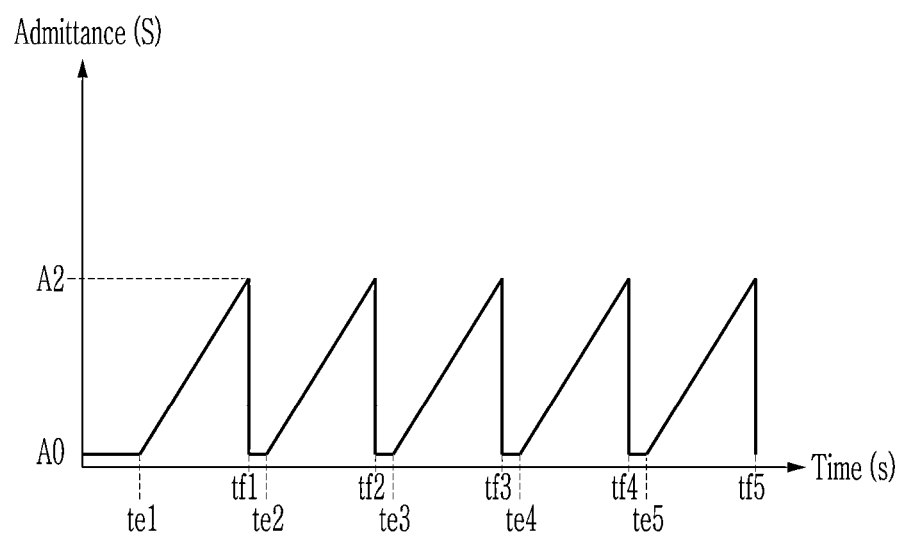
Figure 11:
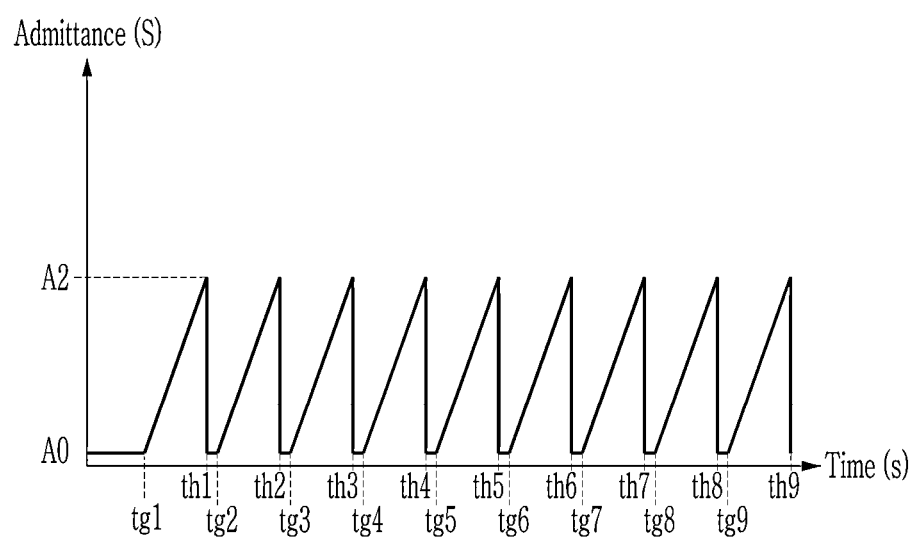

FIG. 8 and FIG. 9 are graphs that show the change of admittance when the sweat ion concentration is high, compared to FIG. 10 and FIG. 11.

FIG. 8 and FIG. 10 are graphs that show the change of admittance when fluid discharge is low, compared to FIG. 9 and FIG. 11.

The period (ta1 to tb1, , ta5 to tb5) from collection to discharge of the body fluid in FIG. 8 is longer than the period (tc1 to td1, tc9 to td9) between collection and discharge of bodily fluid in FIG. 9. That is, when the discharge of the body fluid is large, the period from the time the body fluid is collected and discharged is short. In addition, when the discharge of the body fluid is large, the number of times (5 times in FIGS. 8 and 9 times in FIG. 9) of the rapid admittance changes during the same time period (assuming tb5=td9) is large.

Similarly, the period (te1 to tf1, . . . , te5 to tf5) from collection to discharge of the body fluid at 10 shown in FIG. is longer than the period (tg1 to th1, . . . , tg9 to th9) from collection to discharge of the body fluid shown in FIG. 11. That is, when there is a lot of body fluid secretion, the period from the time the body fluid is collected and discharged is short. In addition, when there is a lot of body fluid secretion, the number of times (5 times in FIGS. 10 and 9 times in FIG. 11) of the admittance changes rapidly during the same time period (assuming that tf5=th9) is large.

In addition, as compared in FIG. 8 and FIG. 9 and in FIG. 10 and FIG. 11, maximum values of admittance vary depending on the composition of the body fluid. That is, the maximum admittance when the ion concentration of the body fluid is low (FIG. 10 and FIG. 11) is lower than the maximum admittance value when the ion concentration of the body fluid is high (FIG. 8 and FIG. 9).

That is, the controller 150 can calculate the ion concentration of the body fluid by using the maximum value of the admittance measured when the admittance changes rapidly. For example, the controller 150 can estimate the ion concentration by using the correlation between the maximum admittance value and the ion concentration. That is, when the maximum value of admittance is measured, the volume of the body fluid in the opening 506 will always be constant, and thus the change in ion concentration in each measurement can be estimated as the maximum value measured when the admittance changes rapidly.

Next, the body fluid sensor of the wearable device will be described in detail with reference to FIG. 12 to FIG. 22.

Figure 12:
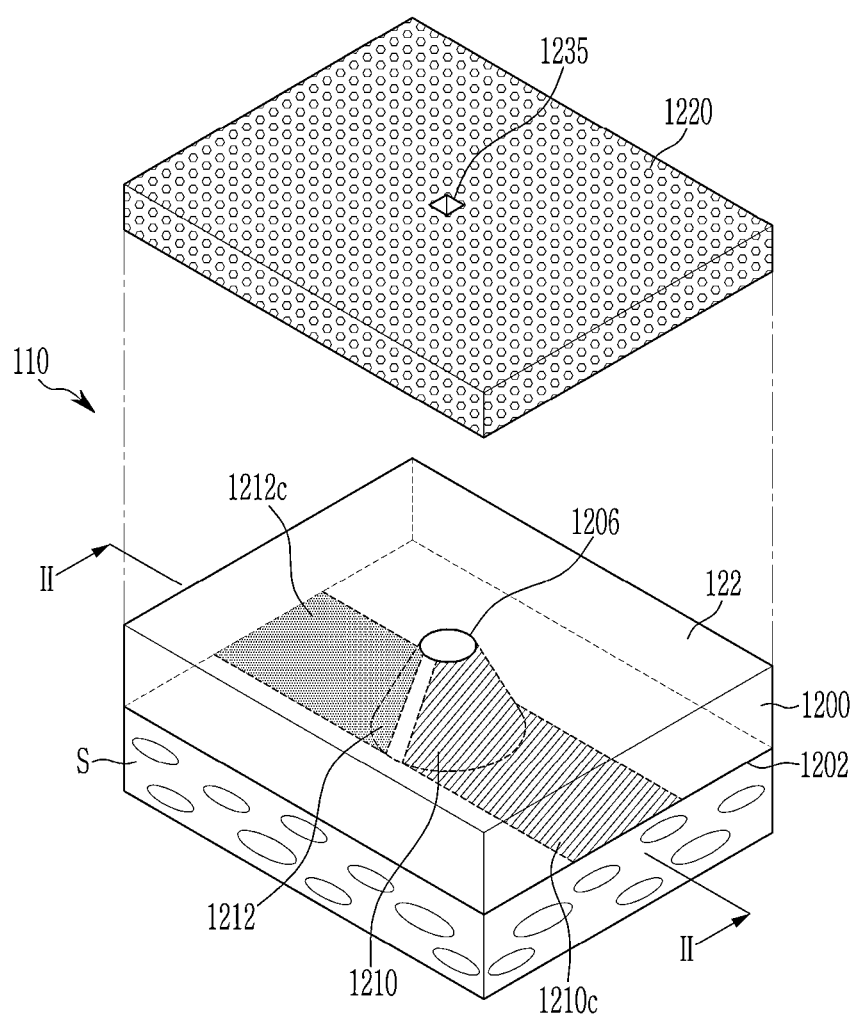
FIG. 12 is an exploded perspective view of a part of an example of the body fluid sensor of the wearable device according to the embodiment.
Figure 13:
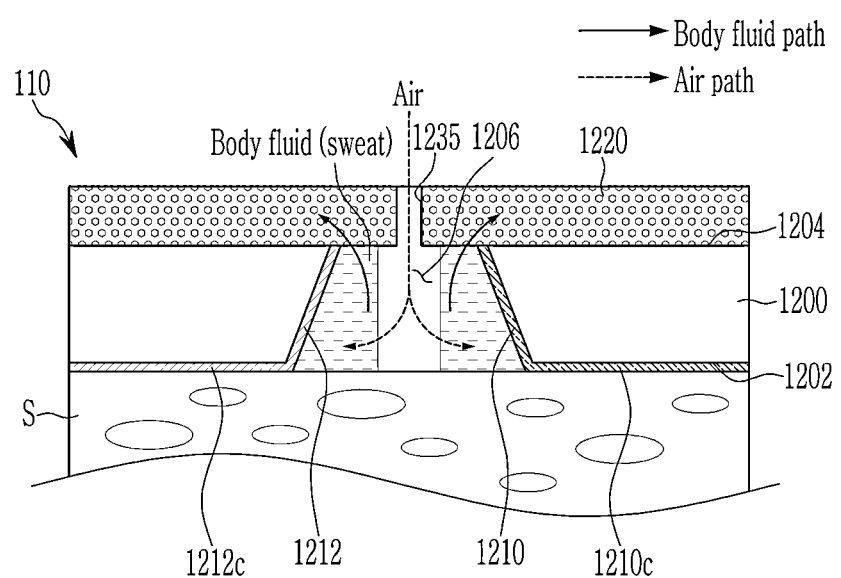
FIG. 13 is a cross-sectional view of a combination of a part of the body fluid sensor shown in FIG. 12, taken along the line II-II.

FIG. 12 is an exploded perspective view of a part of an example of the body fluid sensor of the wearable device according to the embodiment, and FIG. 13 is a cross-sectional view of a combination of a part of the body fluid sensor shown in FIG. 12, taken along the line II-II.

Referring to FIG. 12 and FIG. 13, the body fluid sensor 110 according to the present embodiment is a wearable device that can be used by being attached to the skin S of the user, and includes an opening forming layer 1200 including an opening 1206 that penetrates in a thickness direction, electrodes 1210 and 1212 formed on an inner wall surface of the opening 1206, and a hydrophilic layer 1220 laminated to the opening forming layer 1200. In the present embodiment, the hydrophilic layer 1220 may include an air hole 1235 that penetrates to correspond to the opening 1206.

The opening forming layer 1200 has a first face 1202 and a second face 1204 facing opposite directions, and the opening 1206 can be penetrated through the thickness direction from the first face 1202 to the second face 1204. Here, the first surface 1202 may be a surface attached to the user's skin S, and the second surface 1204 may be a surface facing the outside. Accordingly, the opening 1206 may provide a passage through which the body fluid collected from the first side 1202 attached to the skin S is discharged to the second side 1204. The opening forming layer 1200 may be formed of, for example, a silicone material such as poly(dimethylsiloxane) (PDMS), Ecoflex®, a polymer, a resin, a polyimide, and the like.

In the present embodiment, the opening 1206 may be formed to have a truncated circular cone shape of which a diameter becomes narrower from the first side 1202 to the second side 1204. That is, the flat area of the lateral cross-section of the opening 1206 cut on a plane that is perpendicular to the thickness direction of the opening forming layer 1200 may be larger as it is closer to the first surface 1202 and smaller as it is closer to the second surface 1204. As such, as the diameter of the opening 1206 decreases from the first surface 1202 side, which is the body fluid inlet, to the second surface 1204 side, the dead volume may decrease.

In the above description, the opening 1206 is formed to have a truncated circular cone shape of which a diameter becomes narrower from the first face 1202 to the second face 1204, but the opening 1206 may have a shape of a circular cylinder, a polygonal prism, or a column in which at least a portion is curved, a entasis shape, or a truncated pyramid shape in which at least a part has a curved surface, but is not limited thereto.

The electrodes 1210 and 1212 are formed on the inner wall surface of the opening 1206 to detect a body fluid component. The electrodes 1210 and 1212 can collect quantitative or qualitative data of a body fluid by measuring the flow rate or production speed of the body fluid, and the ion concentration and component of the body fluid. For example, the electrodes 1210 and 1212 may include a nano-mesh electrode made of silver nanowire (Ag NW), a single-walled carbon nanotube (SWNT), or a gold-plated nano-mesh electrode, and a gold thin film or gold plated conductive thin film.

The electrodes 1210 and 1212 are formed on the inner wall surface of the opening 1206 and may extend to a predetermined height. For example, the electrodes 1210 and 1212 may extend from the first side 1202 to the second side 1204. The electrodes 1210 and 1212 may be disposed in any area between the first surface 1202 and the second surface 1204 of the inner wall surface of the opening 1206. The electrodes 1210 and 1212 may be provided in a form surrounded along the inner wall surface of the opening 1206.

The hydrophilic layer 1220 is stacked on the second side 1204 of the opening forming layer 1200, and may be formed to cover the opening 1206. The hydrophilic layer 1220 may include a hydrophilic material. Therefore, the body fluid collected in the opening 1206 can be guided to be discharged more smoothly to the second surface 1204 of the opening forming layer 1200. The hydrophilic layer 1220 may include, for example, a CNT-PDMS (Carbon Nanotube-Poly (dimethylsiloxane)) sponge, a hydrophilic latex sponge, or a hydrophilic polyurethane sponge. The hydrophilic layer 1220 may be a porous layer. Alternatively, the hydrophilic layer 1220 may include a channel forming layer in which channels are formed. The hydrophilic layer 1220 is stacked on the second side 1204 of the opening forming layer 1200, and may have air holes 1225 that penetrate to correspond to the openings 1206. A flat area of the air hole 1225 of the hydrophilic layer 1220 may be formed smaller than a minimum flat area of the opening 1206 of the opening forming layer 1200. External air may be inflowed into the opening 1206 through the air hole 1225.

Figure 14:
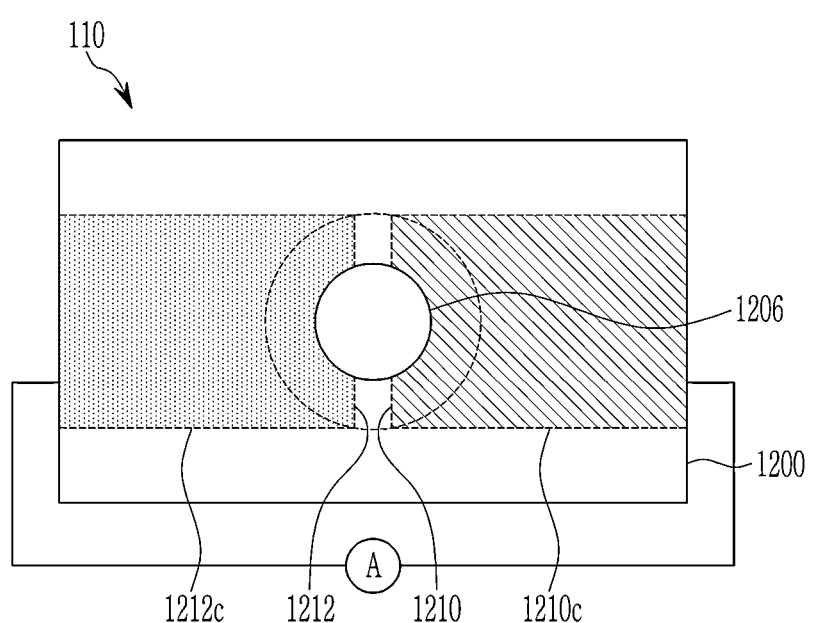
FIG. 14 is a top plan view of electrode connection configuration by combining a part of the body fluid sensor illustrated in FIG. 12.

FIG. 14 is a top plan view of electrode connection configuration by combining a part of the body fluid sensor illustrated in FIG. 12.

Referring to FIG. 14, the electrode 1212 may be disposed to face the electrode 1210 on one side of and opening 1206, and may be formed as a pair with the electrode 1210. As described, the first electrode 1212 is paired with the electrode 1210 to measure the admittance of the bodily fluid filled in the opening 1206, and can sense various information such as concentration, flow rate, and concentration of a specific ion.

The first electrode 1212 and the second electrode 1210 patterned on the inner wall surface of the opening 1206 of the opening forming layer 1200 may be respectively connected to interconnection electrodes 1210c and 1212c formed by extending in one direction from the first surface 1202 of the opening forming layer 1200. The interconnection electrodes 1210c and 1212c may be formed to be connected to an external sensing circuit, thereby connecting the first electrode 1212 to the second electrode 1210.

Next, another example of the body fluid sensor will be described with reference to FIG. 15 to FIG. 17.

Figure 15:
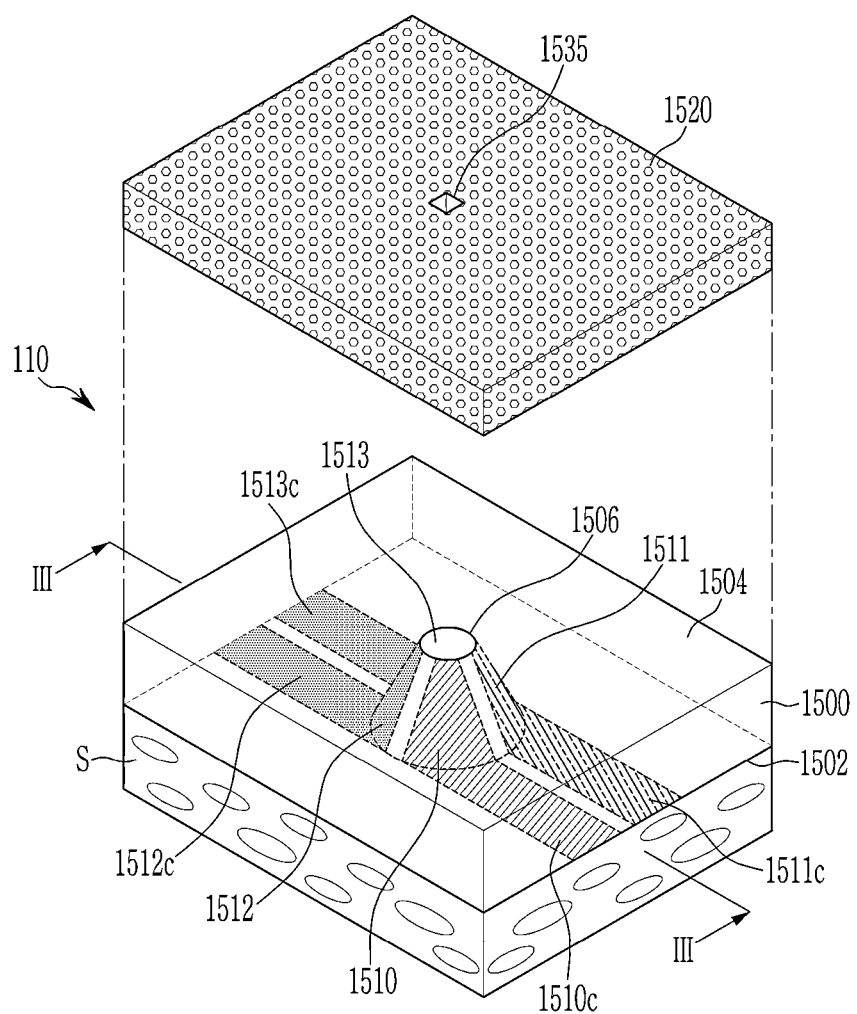
FIG. 15 is an exploded perspective view of a part of another example of the body fluid sensor of the wearable device according to the embodiment.
Figure 16:
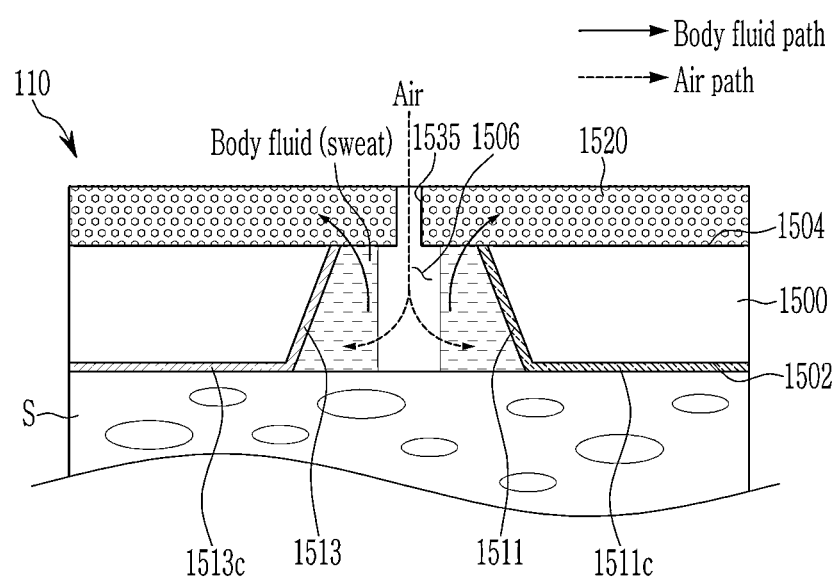
FIG. 16 is a cross-sectional view of combination of the part of the body fluid sensor shown in FIG. 15, taken along the line III-Ill.

FIG. 15 is an exploded perspective view of a part of another example of the body fluid sensor of the wearable device according to the embodiment, and FIG. 16 is a cross-sectional view of combination of the part of the body fluid sensor shown in FIG. 15, taken along the line III-III.

In the descriptions of a body fluid sensor 110 according to the present embodiment, description of the same or similar parts as the body fluid sensor according to the embodiment of FIG. 12 to FIG. 14 will be omitted. Note that reference numbers are updated to correspond to FIG. 15, even if those descriptions are omitted (e.g., hydrophilic layer 1220 is indicated as hydrophilic layer 1520, air hole 1235 is indicated as air hole 1535, etc.).

Electrodes 1510, 1511, 1512, and 1513 are formed on an inner wall surface of an opening 1506 to detect sweat. The electrodes 1510, 1511, 1512, and 1513 may be operated in pairs. For example, the electrode 1510 and the electrode 1512 may form a pair to measure current, and the electrode 1511 and the electrode 1513 may form a pair to measure current. Hereinafter, for convenience of description, the electrodes 1510 and 1511 are referred to as reference electrodes, and the electrodes 1512 and 1513 are referred to as working electrodes.

The number of such electrode pairs may be two or more. Any one of the two electrodes forming the pair may include an electrode for detecting a specific material in the body fluid. For example, any one of the two electrodes forming a pair may include an ion selective electrode (ISE) formed on the electrode through surface treatment. In addition, any one of the two electrodes forming the pair may include an electrode for detecting a specific component (e.g., glucose) of the body fluid.

In the above description, it has been described that the reference electrodes respectively corresponding to a single working electrode are disposed, but the reference electrode may be formed of one electrode. In this case, the body fluid sensor 110 may measure the current by operating it with one working electrode and one reference electrode pair among the two working electrodes.

The electrodes 1510, 1511, 1512, and 1513 are formed on the inner wall surface of the opening 1506, and may extend from a first surface 1502 to a second surface 1504. The first working electrode 1512 and the second working electrode 1513 may be formed to be spaced apart from each other at one side of the inner wall surface of the opening 1506. The first reference electrode 1510 and the second reference electrode 1511 may be formed to be spaced apart from each other at the other side of the inner wall surface of the opening 1506. Accordingly, the electrodes 1510, 1511, 1512, and 1513 may be provided in a form surrounded along the inner wall surface of the opening 1506.

Figure 17:
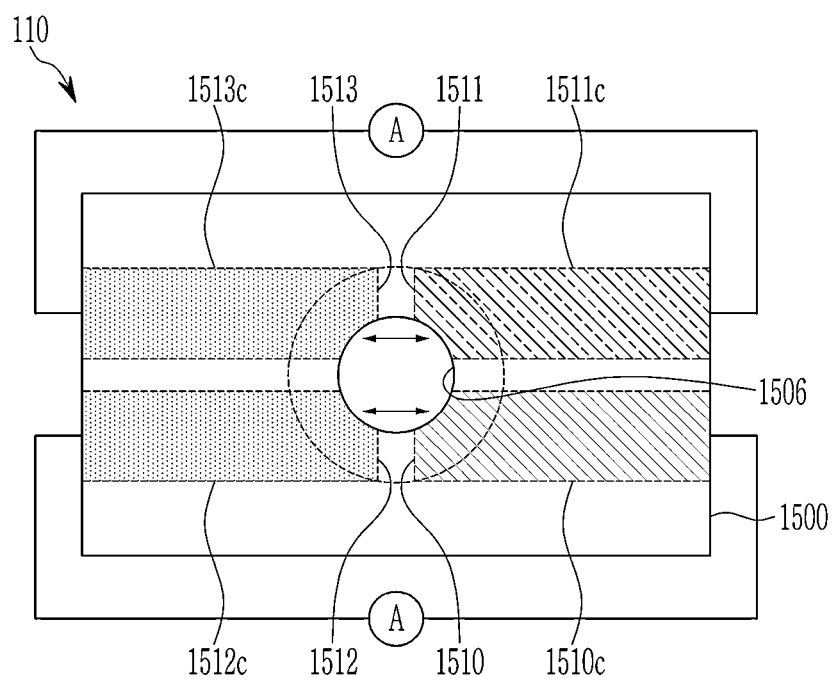
FIG. 17 is a top plan view of an electron connection configuration by combining unit structures of the body fluid sensor illustrated in FIG. 15.

FIG. 17 is a top plan view of an electron connection configuration by combining unit structures of the body fluid sensor illustrated in FIG. 15.

Referring to FIG. 17, the first working electrode 1512 may be disposed to face the first reference electrode 1510 on one side of the opening 1506 and form a pair, and the second working electrode 1513 may be disposed to face the second reference electrode 1511 on the other side of the opening 1506 and form a pair. As such, the working electrodes 1512 and 1513 are paired with the reference electrodes 1510 and 1511 to measure admittance of the bodily fluid filled in the opening 1506, and may sense various information such as a concentration, a flow rate, a concentration of specific ions, and glucose concentration according to various combinations of the working electrodes 1512 and 1513. For example, the first working electrode 1512 may be a K+ ion selective electrode, and the second working electrode 1513 may be a Na+ ion selective electrode.

The first reference electrode 1510, the second reference electrode 1511, the first working electrode 1512, and the second working electrode 1513 patterned on the inner wall surface of the opening 1506 of the opening forming layer 1500 may be respectively connected to interconnection electrodes 1510c, 1511c, 1512c, and 1513c formed by extending in one direction from the first side 1502 of the opening forming layer 1500. The interconnection electrodes 1510c, 1511c, 1512c, and 1513c are connected with an external sensing circuit to connect the first working electrode 1512 to the first reference electrode 1510, and the second working electrode 1513 to the second reference electrode 1511.

Next, referring to FIG. 18 to FIG. 22, another example of the body fluid sensor will be described.

Figure 18:
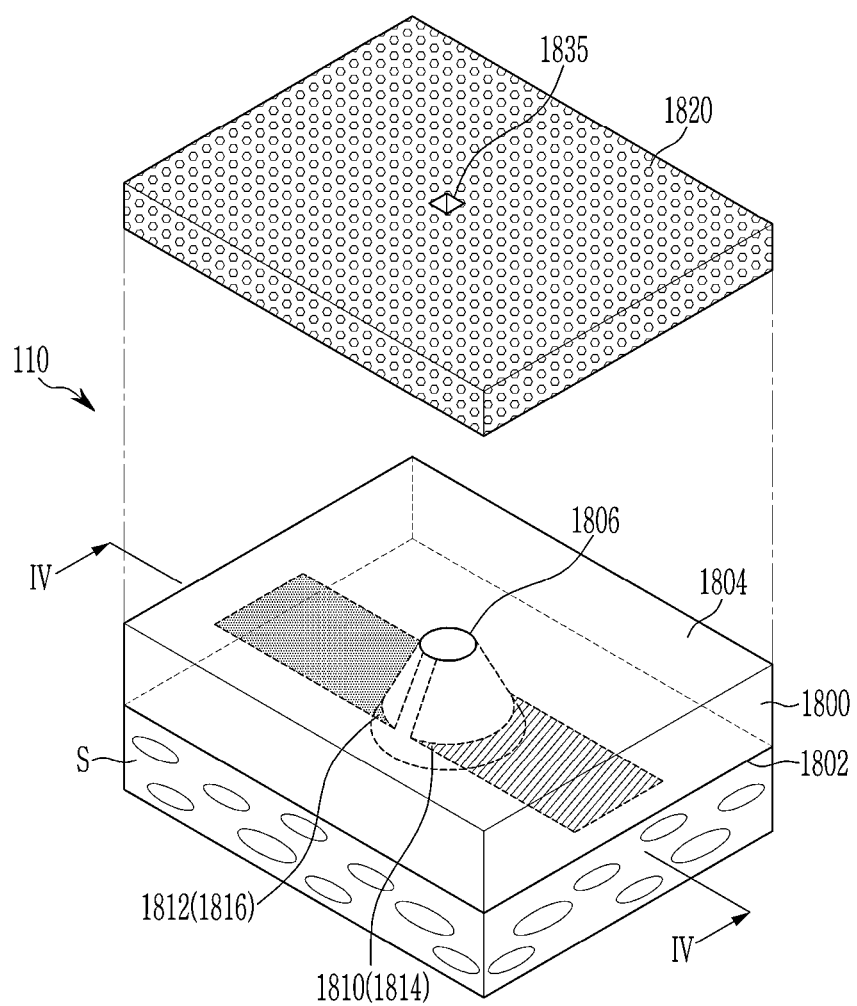
FIG. 18 is an exploded perspective view of a part of another example of the body fluid sensor of the wearable device according to the embodiment.
Figure 19:
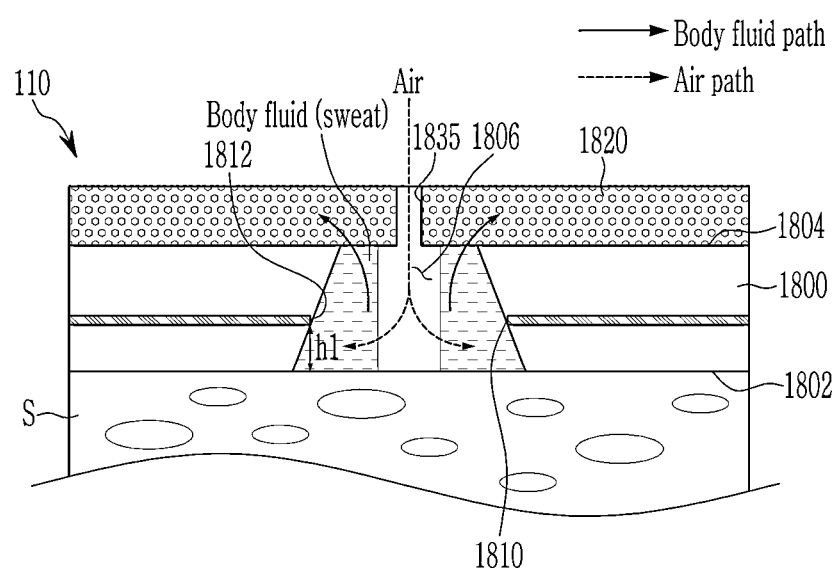
FIG. 19 is a cross-sectional view of combination of the part of the body fluid sensor shown in FIG. 18, taken along the line IV-IV.
Figure 21:
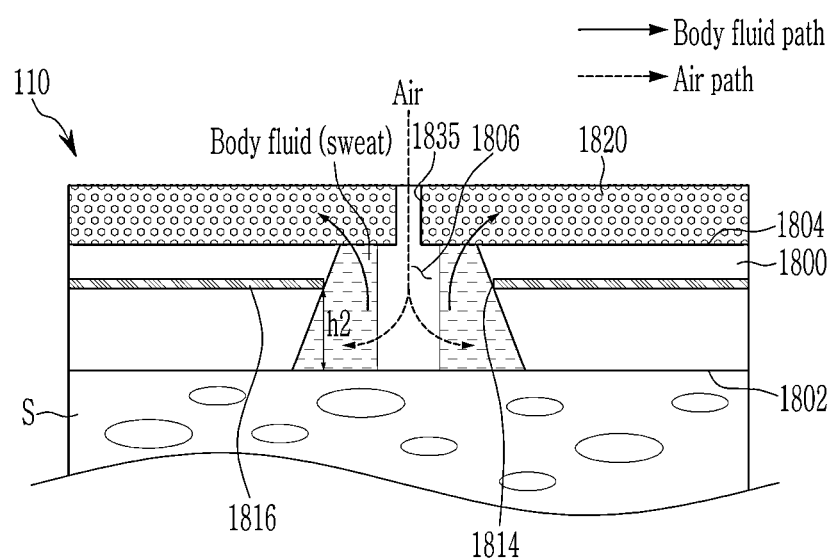
FIG. 21 is a cross-sectional view of combination of the part of the body fluid sensor shown in FIG. 18, taken along the line IV-IV.

FIG. 18 is an exploded perspective view of a part of another example of the body fluid sensor of the wearable device according to the embodiment, and FIG. 19 and FIG. 21 are cross-sectional views of combination of the part of the body fluid sensor shown in FIG. 18, taken along the line IV-IV.

In the descriptions of a body fluid sensor 110 according to the present embodiment, description of the same or similar parts as the body fluid sensor according to the embodiment of FIG. 12 to FIG. 14 will be omitted. Note that reference numbers are updated to correspond to FIG. 18, even if those descriptions are omitted (e.g., hydrophilic layer 1220 is indicated as hydrophilic layer 1820, air hole 1235 is indicated as air hole 1835, second face 1204 is indicated as second face 1804, opening forming layer 1200 is indicated as opening forming layer 1800, etc.).

A body fluid sensor of FIG. 19 and a body fluid sensor of FIG. 21 are respectively illustrated as individual examples of the body fluid sensor. The body fluid sensor of FIG. 19 and the body fluid sensor of FIG. 21 may be respectively located in different portions of a single wearable device.

Referring to FIG. 19, electrodes 1810 and 1812 are formed on an inner wall surface of an opening 1806 to detect sweat. The electrodes 1810 and 1812 may be disposed on the inner wall surface of the opening 1806 at a first height h1 from a first surface 1802. The height of the two electrodes 1810 and 1812 may be disposed at the same height, but is not limited thereto. The electrodes 1810 and 1812 may be provided in a form surrounded along the inner wall surface of the opening 1806.

Referring to FIG. 21, electrodes 1814 and 1816 are also formed on an inner wall surface of an opening 1806 to detect sweat. The electrodes 1814 and 1816 may be disposed on the inner wall surface of the opening 1806 at a second height h2 from the first surface 1802. The two electrodes 1814 and 1816 may be disposed at the same height, but are not limited thereto. The electrodes 1814 and 1816 may be provided in a form surrounded along the inner wall surface of the opening 1806.

The heights h1 and h2 at which the electrodes 1810 and 1812 and the electrodes 1814 and 1816 are disposed in each body fluid sensor 110 included in one wearable device 10 may be different from each other.

Figure 20:
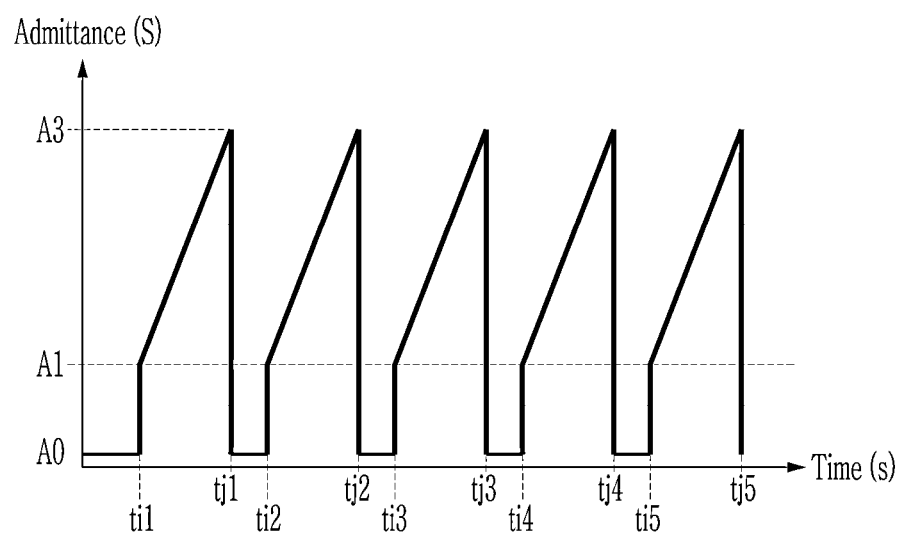
FIG. 20 is a graph showing the change in admittance measurement value according to the body fluid collection of the body fluid sensor of FIG. 19.
Figure 22:
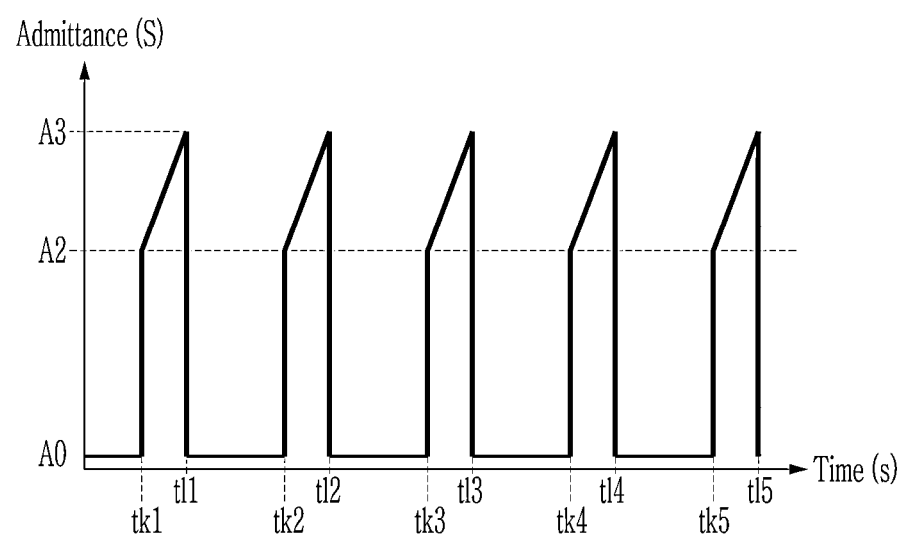
FIG. 22 is a graph showing the change in admittance measurement value according to the body fluid collection of the body fluid sensor of FIG. 21.

FIG. 20 is a graph showing the change in admittance measurement value according to the body fluid collection of the body fluid sensor of FIG. 19, and FIG. 22 is a graph showing the change in admittance measurement value according to the body fluid collection of the body fluid sensor of FIG. 21.

Referring to FIG. 20, a sharply increased admittance (increasing from A0 to A1) is measured at time ti1 when the body fluid reaches the first height h1 in the opening 1806. Thereafter, the admittance gradually increases as the body fluid is discharged, and the body fluid is discharged at time tj1. Even in this case, the controller 150 may count the number of times the admittance sharply decreases during a certain period of time.

Referring to FIG. 22, the admittance rapidly increased (increasing from A0 to A2) at time tk1 when the body fluid has reached the first height h2 in the opening 1806 is measured. Thereafter, the admittance gradually increases as the body fluid is discharged, and the body fluid is discharged at time tl1. Even in this case, the controller 150 may count the number of times the admittance sharply decreases during a certain period of time.

When the same flow rate of body fluid is discharged, compared to the body fluid sensor of FIG. 21, the body fluid sensor of FIG. 19 has a higher sensitivity for body fluid detection. That is, compared to the body fluid sensor of FIG. 21, the body fluid sensor of FIG. 19 can detect a lower flow rate of body fluid.

Figure 23:
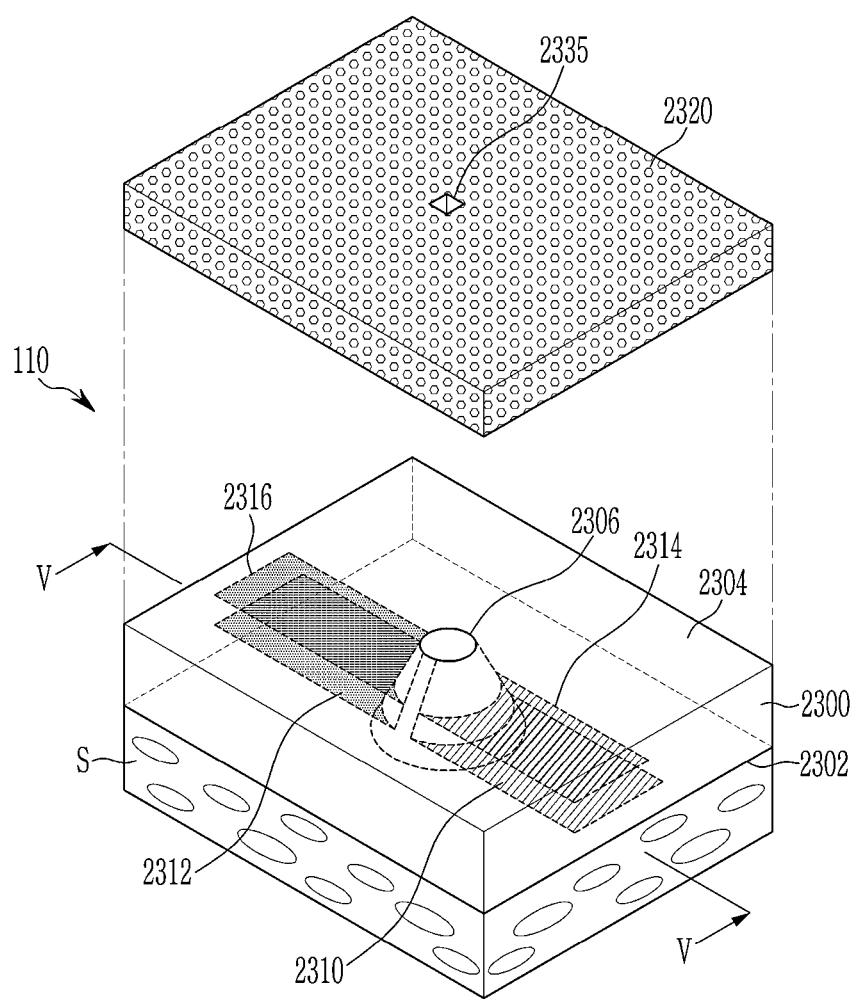
FIG. 23 is an exploded perspective view of a part of another example of the body fluid sensor of the wearable device according to the embodiment.
Figure 24:
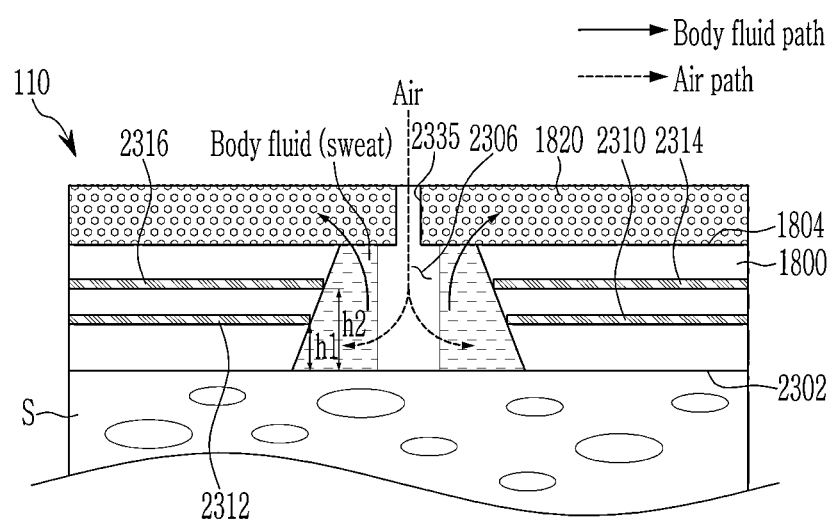
FIG. 24 is a cross-sectional view of combination of the part of the body fluid sensor shown in FIG. 23, taken along the line V-V.

FIG. 23 is an exploded perspective view of a part of another example of the body fluid sensor of the wearable device according to the embodiment, and FIG. 24 is a cross-sectional view of combination of the part of the body fluid sensor shown in FIG. 23, taken along the line V-V. In the descriptions of a body fluid sensor 110 according to the present embodiment, description of the same or similar parts as the body fluid sensor according to the embodiment of FIG. 12 to FIG. 14 will be omitted. Note that reference numbers are updated to correspond to FIG. 23, even if those descriptions are omitted (e.g., hydrophilic layer 1220 is indicated as hydrophilic layer 2320, air hole 1235 is indicated as air hole 2335, second face 1204 is indicated as second face 2304, opening forming layer 1200 is indicated as opening forming layer 2300, etc.).

Electrodes 2310, 2312, 2314, and 2316 are formed on an inner wall surface of the opening 2306 to detect sweat. Electrodes 2310 and 2312 may be disposed on the inner wall surface of the opening 2306 at a first height h1 from a first surface 2302. The height of the two electrodes 2310 and 2312 may be the same, but is not limited thereto. The electrodes 2310 and 2312 may be provided in a form surrounded along the inner wall surface of the opening 2306.

The electrodes 2314 and 2316 may be disposed on the inner wall surface of the opening 2306 at a second height h2 from the first surface 2302. The heights of the two electrodes 2314 and 2316 may be the same height, but are not limited thereto. The electrodes 2314 and 2316 may be provided in a form surrounded along the inner wall surface of the opening 2306.

Since the body fluid sensor of the present embodiment includes the electrodes 2310, 2312, 2314, and 2316 disposed at the first height h1 and the second height h2 within the opening 2306, different electrode pairs can be used to measure the admittance depending on the admittance change or the state of the wearable device 10.

When a value measured by other sensors (for example, the pulse sensor 114) in the wearable device 10 changes, the body fluid sensor 110 may select one of the two electrode pairs to measure the admittance. For example, when the pulse rate measured by the pulse sensor 114 is 130 beats per minute or more, the electrodes 2314 and 2316 having a higher second height h2 may be driven. That is, when the discharge of body fluid is active, the electrodes 2314 and 2316 disposed at a high position are driven. In addition, when the pulse rate measured by the pulse sensor 114 is less than 130 beats per minute, the electrodes 2310 and 2312 having a lower first height h1 may be driven. That is, when the discharge of the body fluid is not active, the electrodes 2310 and 2312 disposed at a low position are driven.

Alternatively, the body fluid sensor 110 drives the electrodes 2310 and 2312 of the first height h1 and the electrodes 2314 and 2316 of the second height h2 immediately after the body fluid is removed, respectively, and when the admittance values are different, the electrodes 2314 and 2316 of the second height h2 are driven, and when the admittance values are the same, the electrodes 2310 and 2312 having the first height h1 can be driven. That is, after the body fluid is removed, whether the body fluid is less than the first height h1 or the second height h2 is measured using two electrode pairs, and then admittance can be measured by selecting one of the two electrode pairs.

In the case of the electrodes 2314 and 2316 of the second height h2, the difference between the maximum value measured immediately before body fluid removal and the minimum value measured immediately after body fluid removal is larger than that of the electrodes 2310 and 2312 of the first height h1. Therefore, the electrodes 2314 and 2316 of the second height h2 have better SNR for admittance change than the electrodes 2310 and 2312 of the first height h1.

Next, referring to FIG. 25 to FIG. 27, a method for controlling a wearable device according to an embodiment will be described.

Figure 25:
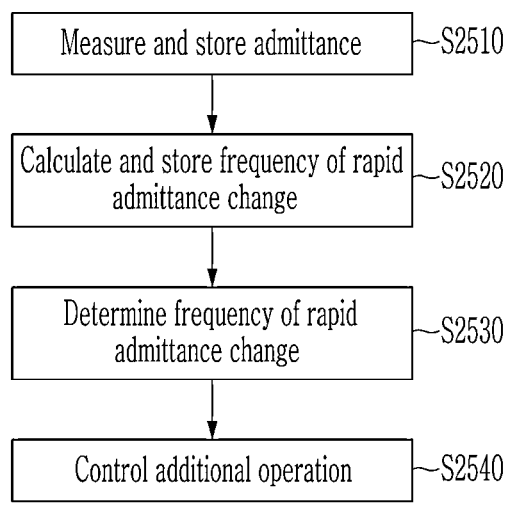
FIG. 25 is a flowchart of a control method of a wearable device according to an embodiment.

FIG. 25 is a flowchart of a control method of a wearable device according to an embodiment.

Referring to FIG. 25, a body fluid sensor 110 of a wearable device 10 measures admittance according to discharge of body fluid, and a memory 130 stores an admittance measured value of the body fluid sensor 110 (S2510).

The admittance measured by the body fluid sensor 110 may be converted into a digital value through an ADC converter included in the body fluid sensor 110 and/or the controller 150 and stored in the memory 130.

Then, the controller 150 calculates the frequency at which the admittance changes rapidly and stores it in the memory 130 (S2520).

The controller 150 may calculate the frequency at which the admittance changes rapidly by using the number of times that the admittance value measured by the body fluid sensor 110 sharply decreases during a predetermined period. In addition, the controller 150 can measure a flow rate of the body fluid (e.g., the amount of sweat secretion) using the frequency of rapid change in admittance.

The controller 150 determines the increase or decrease of the frequency of rapid change in admittance (S2530). For example, when an interval between a first time point and a second time point when the admittance changes rapidly is 140 seconds, and an interval between a third time point and the second time point where the admittance changes rapidly after the second time point is 20 seconds, the controller 150 determines that the frequency of rapid change in admittance has increased. Alternatively, the controller 150 may determine an increase or decrease in the frequency of rapid change in admittance by comparing the number of times the admittance changes rapidly during a predetermined period. Referring to FIG. 26, the change in the admittance measured value according to the fluid flow rate will be described.

Figure 26:
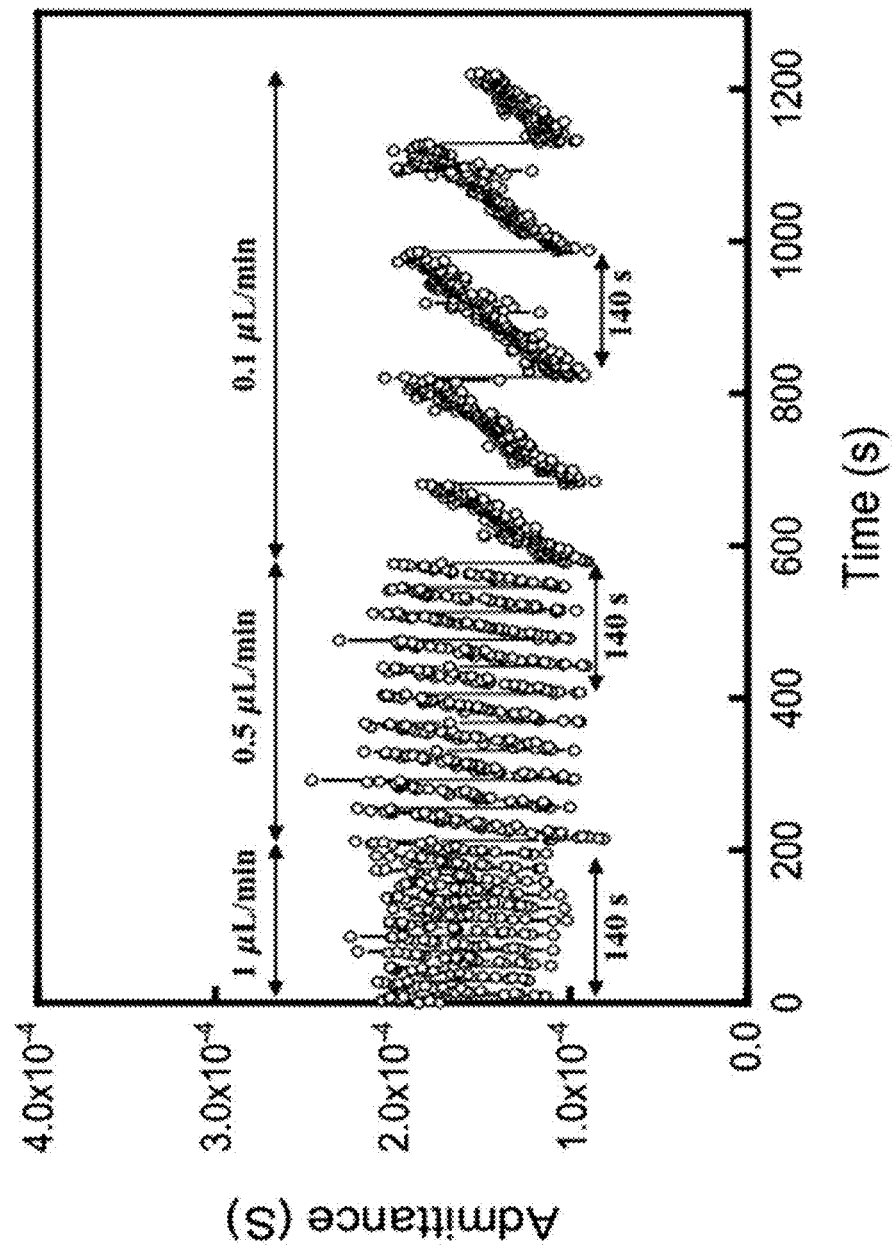
FIG. 26 is a graph showing an actual measurement value of admittance according to collection of body fluid of the wearable device according to the embodiment.

FIG. 26 is a graph showing an actual measurement value of admittance according to collection of body fluid of the wearable device according to the embodiment.

As shown in FIG. 26, the flow rate of the body fluid is increased as the number of times the admittance changes rapidly during the same period of 140 seconds is increased.

Meanwhile, the controller 150 may measure the ion concentration (e.g., Na+ ion concentration and/or K+ ion concentration) of the body fluid by using the maximum admittance value measured by the body fluid sensor 110.

Figure 27:
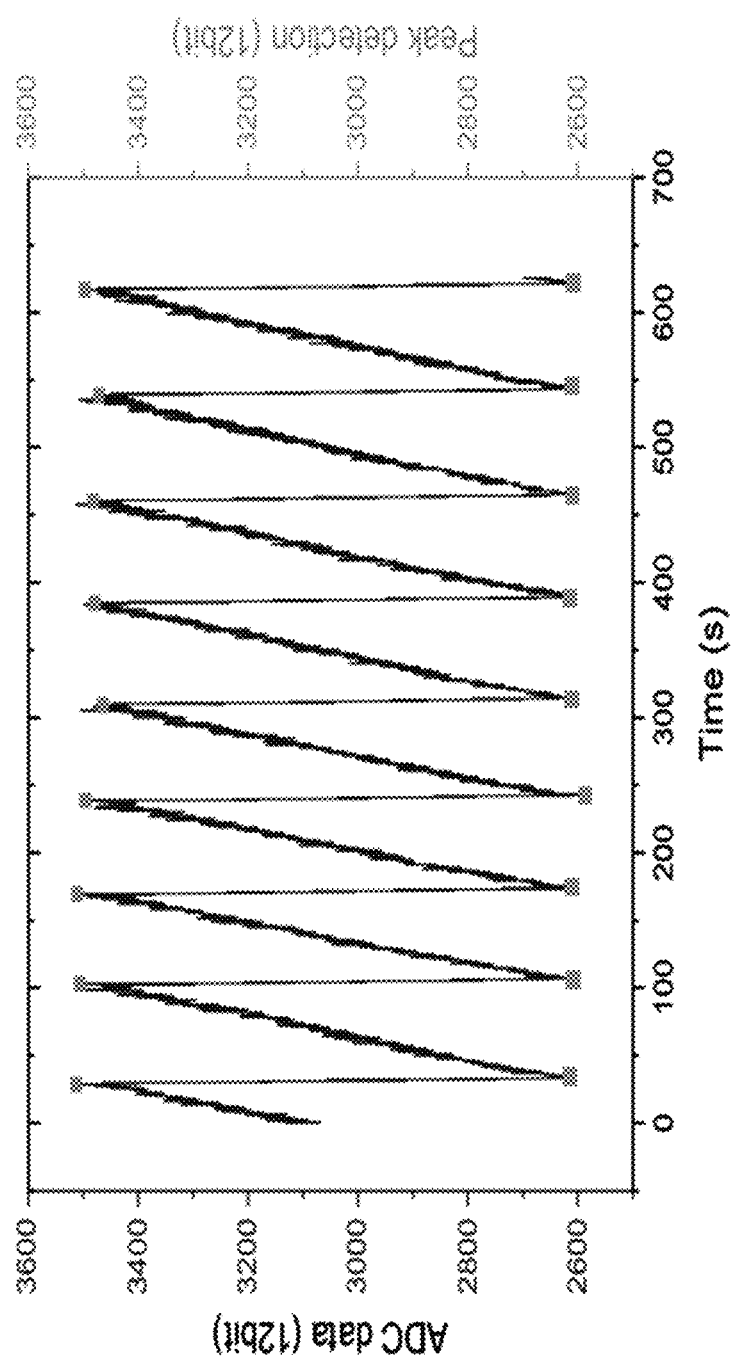
FIG. 27 is a graph showing the maximum and minimum values of the admittance actual measured values according to the collection of the body fluid of the wearable device according to the embodiment.

FIG. 27 is a graph showing the maximum and minimum values of the admittance actual measured values according to the collection of the body fluid of the wearable device according to the embodiment.

As shown in FIG. 27, the admittance value changes according to body fluid discharge.

Next, the controller 150 controls an additional operation according to the increase or decrease of the frequency of rapid change of admittance (S2540). In this case, with respect to the increase or decrease of the frequency of rapid change of admittance, the controller 150 may determine that the amount of body fluid discharge (flow rate) increases in all cases where the frequency increases with time. Similarly, the controller 150 may determine all cases where the frequency decreases with time as a decrease in body fluid discharge (flow rate).

In addition, the controller 150 may determine that the amount of body fluid discharge (flow rate) increases when the number of rapid changes in admittance measured during a predetermined period increases by a predetermined number or more.

In addition, the controller 150 may determine whether the number of rapid changes in admittance measured for a predetermined period is included in a plurality of sections, and may control an additional operation according to each section. For example, the controller 150 determines whether the number of rapid changes is included in the interval of once or more and less than 2 times per 120 seconds, 2 or more and less than 4 times per 120 seconds, and 4 or more and less than 8 times per 120 seconds, and may initiate the corresponding operation.

In addition, the controller 150 may determine whether the calculated amount of body fluid discharge (flow rate) is included in a plurality of sections, and may control additional operations according to each section. For example, the controller 150 determines whether the body fluid discharge (flow rate) is included in a 0 to 0.1 (µl/min) section, a 0.1 to 0.5 (µl/min) section, and a 0.5 to 1 (µl/min) section, and may initiate an operation corresponding to each section.

For example, when the amount of body fluid discharge (flow rate) increases (or when the frequency of rapid change in admittance increases), the controller 150 operates the bioelectric sensor 112 to detect and monitor at least one of electrocardiogram (ECG) and electromyogram (EMG).

As another example, when the amount of body fluid discharge (flow rate) increases (or when the frequency of rapid change in admittance increases), the controller 150 operates the wireless communication portion 120 to transmit the frequency of rapid change in admittance and the maximum value A3 and minimum value A0 of admittance to the external electronic device 20.

As another example, whenever the admittance changes rapidly, the controller 150 transmits a sudden change signal to the external electronic device 20. The controller 150 may transmit the maximum and minimum values of the admittance measured before and after the timing when the admittance changes rapidly as a sudden change signal to the external electronic device 20. Then, whenever the electronic device 20 receives the sudden change signal, it is possible to calculate the frequency of the rapid change of admittance, and through this, the flow rate of the body fluid can be calculated, and the ion concentration of the body fluid can be calculated from the maximum value of the admittance. In addition, the wearable device 10 may transmit the maximum admittance value A3, and a ratio (A3/(A3-A0)) of the maximum value A3 and a difference between the maximum value A3 and the minimum value A0 to the external electronic device 20 as a sudden change signal.

As another example, the controller 150 only wirelessly transmits the frequency of rapid change in admittance measured by the body fluid sensor 110, and the maximum admittance value A3, and a ratio (A3/(A3-A0)) of the maximum value A3 and a difference between the maximum value A3 and the minimum value A0 to the external electronic device 20 through the communication portion 120. When body fluid discharge (flow rate) increases (or when the frequency of rapid changes in admittance increases), the controller 150 transmits the entire admittance measurement value measured from when the admittance sudden change frequency increased, the frequency of rapid changes in admittance, and the ratio (A3/(A3-A0)) of the maximum value A3 and the difference between the maximum value A3 and the minimum value A0 to the external electronic device 20 through the wireless communication portion 120.

As another example, the controller 150 transmits the entire ECG curved line data measured by the bioelectric sensor 112 to the external electronic device 20 through the wireless communication portion 120 when the amount of body fluid (flow) increases (or the frequency of abrupt change in admittance increases).

As another example, the controller 150 extracts R peak data of an ECG curve measured by the bioelectric sensor 112 and transmits the extracted data to the external electronic device 20 through the wireless communication portion 120.

The controller 150 transmits the entire ECG curve data measured by the bioelectric sensor 112 to the external electronic device 20 through the wireless communication portion 120 when the amount of body fluid (flow rate) increases (or the frequency of abrupt change in admittance increases).

As another example, when the amount of body fluid (flow rate) increases (or the frequency of a sudden change in admittance increases), the controller 150 operates the pulse sensor 114 to initiate detection and monitoring of the user's pulse.

As another example, when the amount of body fluid (flow rate) increases (or the frequency of a rapid change in admittance increases), the controller 150 transmits the pulse data measured by the pulse sensor 114 to the external electronic device 20 through the wireless communication portion 120.

As another example, when the amount of body fluid (flow rate) increases (or the frequency of a rapid change in admittance increases), the controller 150 transmits the data measured by the bioelectric sensor 112 and the pulse sensor 114 to the external electronic device 20 through the wireless communication portion 120.

As another example, the controller 150 stores only the frequency of rapid change and the maximum and minimum values of the admittance measured by the body fluid sensor 110 in the memory 130. When the amount of body fluid (flow rate) increases (or when the frequency of rapid change in admittance increases), the controller 150 stores body fluid flow information (measured admittance), the frequency of rapid change in admittance, and the maximum and minimum values, in the memory 130.

As another example, when the amount of body fluid (flow rate) increases (or the frequency of a rapid change in admittance increases), the controller 150 may operate various sensors (biological sensor, acceleration sensor sensing the wearer's physical characteristics, temperature sensor, altitude sensor, motion sensor, position sensor, and the like) or units included in the wearable device 10.

As described above, when the amount of body fluid (flow rate) increases (or when the frequency of rapid change in admittance increases), the controller 150 may transmit the measured information to the electronic device 20 such that the electronic device 20 outputs the measured information.

That is, the controller 150 controls the communication unit to transmit the conductivity data to the external device 20 in response to the frequency of rapid change in conductivity.

Since body fluid is intermittently secreted, quantitative or qualitative data of most body fluids measured when wearing the wearable device 10 may be redundant or less useful.

According to the present disclosure, power consumption is reduced by initiating data transmission according to the change in admittance frequency, and thus the use time of the wearable device is increased, and a smaller capacity battery to power a storage device can be mounted, thereby providing a smaller and thinner wearable device.

According to the present disclosure, since various data are transmitted according to the change in admittance frequency, there is merit in easy data collection according to the user's physical condition.

According to the present disclosure, since it is easy to remove the body fluid, the user's biological signal can be continuously acquired for a long time.

According to the present disclosure, since the data stored varies according to the change in admittance frequency, there is an effect of reducing the manufacturing cost due to a small memory capacity.

While this invention has been described in connection with what is presently considered to be practical embodiments, it is to be understood that the invention is not limited to the disclosed embodiments. On the contrary, it is intended to cover various modifications and equivalent arrangements included within the spirit and scope of the appended claims.

What is claimed is:

1. A wearable device comprising:
 a communication unit;
 a body fluid sensor configured to measure conductivity in body fluid of a subject wearing the wearable device, the body fluid comprising sweat discharged by the subject; and
 a controller configured to:
  determine a plurality of rapid changes in the conductivity, wherein the rapid change is identified when the measured conductivity changes discretely; and
  control the communication unit to transmit conductivity data to an external device in response to an increase in a frequency of the rapid change in the conductivity based on the plurality of rapid changes, wherein power consumption of the wearable device is reduced by initiating data transmission according to the identification of the rapid changes in the conductivity.

2. The wearable device of claim 1, wherein
 the controller is further configured to control the communication unit to transmit the frequency of the rapid change in conductivity, and a maximum value and a minimum value in rapid change of the conductivity as the conductivity data to the external device.

3. The wearable device of claim 1, wherein
 the controller is further configured to control the communication unit to further include entire conductivity values measured from when the frequency of the rapid change of the conductivity increases in the conductivity data, and transmit the entire conductivity values to the external device.

4. The wearable device of claim 1, further comprising a bioelectric sensor configured to monitor at least one of an electrocardiogram (ECG) and an electromyogram (EMG).

5. The wearable device of claim 4, wherein
 the controller is further configured to control the bioelectric sensor to initiate monitoring with respect to at least one of the ECG and the EMG corresponding to the frequency of the rapid change in conductivity.

6. The wearable device of claim 4, wherein the bioelectric sensor is configured to monitor the ECG, and
 the controller is further configured to extract R peak data in an ECG curved line, measured by the bioelectric sensor, and to transmit, via control of the communication unit, the extracted R peak data to the external device, and to control the communication unit to transmit the ECG curved line to the external device when a flow rate of the body fluid increases.

7. The wearable device of claim 1, further comprising a pulse sensor configured to monitor a pulse.

8. The wearable device of claim 7, wherein
 the controller is further configured to control the pulse sensor to initiate monitoring of the pulse corresponding to the frequency of the rapid change in conductivity.

9. The wearable device of claim 7, wherein
when the frequency of the rapid change in conductivity increases, the controller is further configured to control the communication unit to transmit pulse data comprising the pulse to the external device.

10. The wearable device of claim 1, wherein
the body fluid sensor comprises:
an opening forming layer that includes a first side and a second side respectively facing opposite directions, and an opening penetrating from the first side to the second side in a thickness direction;
a plurality of electrodes formed on an inner wall surface of the opening penetrating from the first side to the second side; and
a hydrophilic layer stacked on the second side of the opening forming layer to cover the opening.

11. The wearable device of claim 10, wherein
each of the plurality of electrodes extends from the first side to the second side on the inner wall surface.

12. The wearable device of claim 10, wherein
each of the plurality of electrodes is disposed at a predetermined height from the first side on the inner wall surface.

13. The wearable device of claim 10, wherein
any one of the plurality of electrodes includes an electrode that detects a specific component in the body fluid.

14. A system comprising:
the wearable device of claim 1; and
an electronic device that outputs data received from the wearable device.

15. The system of claim 14, wherein
when the frequency of the rapid change in the conductivity increases, the wearable device transmits the conductivity data to the electronic device whenever the conductivity rapidly changes, and
the electronic device measures a flow rate of the body fluid by using a time point of receiving the conductivity data.

16. The system of claim 14, wherein:
the wearable device transmits a maximum value of the conductivity as the conductivity data to the electronic device, and
the electronic device calculates an ion concentration of the body fluid by using the maximum value of the conductivity.

17. A control method of a wearable device, comprising:
measuring conductivity of a body fluid of a subject wearing the wearable device by a body fluid sensor, the body fluid comprising sweat discharged by the subject;
determining a plurality of rapid changes in the conductivity, wherein the rapid change is identified when the measured conductivity changes discretely; and
transmitting conductivity data of the body fluid to an external device corresponding to a frequency of the rapid change in conductivity, wherein power consumption of the wearable device is reduced by initiating data transmission according to the identification of the rapid changes in the conductivity.

18. The control method of the wearable device of claim 17, wherein the transmitting of the conductivity data of the body fluid comprises
transmitting the frequency of the rapid change in conductivity, and a maximum value and a minimum value of the conductivity as the conductive data to the external device, or
when the frequency of the rapid change in conductivity is increased, transmitting entire conductive values measured from when the frequency of the rapid change in conductivity increases, and the maximum and minimum values of the conductivity as the conductive data to the external device.

19. The control method of the wearable device of claim 17, further comprising
initiating monitoring with respect to at least one of an electrocardiogram (ECG) and an electromyogram (EMG) corresponding to the frequency of the rapid change in conductivity by a bioelectric sensor.

20. The control method of the wearable device of claim 17, further comprising:
monitoring an electrocardiogram (ECG) by a bioelectric sensor; and
1) extracting R peak data of an ECG curved line and transmitting the extracted R peak data to the external device, or
2) when the frequency of the rapid change in conductivity increases, transmitting the ECG curved line measured by the bioelectric sensor to the external device.

21. The control method of the wearable device of claim 17, further comprising initiating monitoring with respect to a pulse corresponding to the frequency of the rapid change in conductivity by a pulse sensor.

22. The control method of the wearable device of claim 17, further comprising:
monitoring a pulse by a pulse sensor; and
when the frequency of the rapid change in conductivity increases, transmitting pulse data to the external device.

23. The control method of the wearable device of claim 17, wherein the body fluid sensor comprises:
an opening forming layer that includes a first side and a second side respectively facing opposite directions, and an opening penetrating from the first side to the second side in a thickness direction;
a plurality of electrodes formed on an inner wall surface of the opening penetrating from the first side to the second side; and
a hydrophilic layer stacked on the second side of the opening forming layer to cover the opening penetrating from the first side to the second side,
wherein the measuring of the conductivity in the body fluid by the body fluid sensor comprises measuring a current flowing through the plurality of electrodes.

24. The control method of the wearable device of claim 23, further comprising:
calculating a flow rate of the body fluid by using the frequency of the rapid change in the conductivity, a volume of the opening, and a value of the conductivity.

* * * * *